United States Patent
Hoekstra et al.

(10) Patent No.: US 9,802,914 B2
(45) Date of Patent: Oct. 31, 2017

(54) ANTIFUNGAL COMPOUND PROCESS

(71) Applicant: Viamet Pharmaceuticals, Inc., Durham, NC (US)

(72) Inventors: William J. Hoekstra, Durham, NC (US); Christopher M. Yates, Raleigh, NC (US)

(73) Assignee: Viamet Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 15/126,330

(22) PCT Filed: Mar. 19, 2015

(86) PCT No.: PCT/US2015/021436
§ 371 (c)(1),
(2) Date: Sep. 15, 2016

(87) PCT Pub. No.: WO2015/143137
PCT Pub. Date: Sep. 24, 2015

(65) Prior Publication Data
US 2017/0081309 A1   Mar. 23, 2017

Related U.S. Application Data

(60) Provisional application No. 61/955,554, filed on Mar. 19, 2014.

(51) Int. Cl.
| | |
|---|---|
| *C07D 401/06* | (2006.01) |
| *C07D 213/26* | (2006.01) |
| *C07D 213/61* | (2006.01) |
| *A61K 31/4439* | (2006.01) |
| *A61K 45/06* | (2006.01) |
| *C07D 213/30* | (2006.01) |
| *C07D 213/50* | (2006.01) |

(52) U.S. Cl.
CPC ........ *C07D 401/06* (2013.01); *A61K 31/4439* (2013.01); *A61K 45/06* (2013.01); *C07D 213/26* (2013.01); *C07D 213/30* (2013.01); *C07D 213/50* (2013.01); *C07D 213/61* (2013.01)

(58) Field of Classification Search
None
See application file for complete search history.

(56) References Cited

FOREIGN PATENT DOCUMENTS

| | | |
|---|---|---|
| JP | 2000-344744 A | 12/2000 |
| WO | WO 2011/133875 A2 | 10/2011 |
| WO | WO 2012/177608 A1 | 12/2012 |
| WO | WO 2012/177635 A1 | 12/2012 |
| WO | WO 2012/177725 A1 | 12/2012 |
| WO | WO 2012/177728 A1 | 12/2012 |
| WO | WO 2013/109998 A1 | 7/2013 |
| WO | WO 2013/110002 A1 | 7/2013 |

OTHER PUBLICATIONS

International Search Report and Written Opinion mailed Jun. 25, 2015 for Application No. PCT/US2015/021436.
International Search Report and Written Opinion mailed Jun. 29, 2015 for Application No. PCT/US2015/021445.
International Search Report and Written Opinion mailed Jun. 26, 2015 for Application No. PCT/US2015/021519.
International Search Report and Written Opinion mailed Jun. 29, 2015 for Application No. PCT/US2015/021527.
International Search Report and Written Opinion mailed Jul. 14, 2015 for Application No. PCT/US2015/021464.
International Search Report and Written Opinion mailed Jul. 14, 2015 for Application No. PCT/US2015/021476.
International Search Report and Written Opinion mailed Jul. 10, 2015 for Application No. PCT/US2015/021484.
International Search Report and Written Opinion mailed Jun. 24, 2015 for Application No. PCT/US2015/021491.
International Search Report and Written Opinion mailed Jun. 26, 2015 for Application No. PCT/US2015/021504.
International Search Report and Written Opinion mailed Jun. 24, 2015 for Application No. PCT/US2015/021511.

*Primary Examiner* — Zinna Northington Davis
(74) *Attorney, Agent, or Firm* — Wolf, Greenfield & Sacks, P.C.

(57) ABSTRACT

The present invention relates to a process for preparing compound 1 that is useful as an antifungal agent. In particular, the invention seeks to provide new methodology for preparing compound 1 or 1a and substituted derivatives thereof.

10 Claims, No Drawings

ANTIFUNGAL COMPOUND PROCESS

CROSS REFERENCE TO RELATED APPLICATIONS

This application is the U.S. National Stage, pursuant to 35 U.S.C. §371, of International Application No. PCT/US2015/021436, filed Mar. 19, 2015, which claims the benefit of U.S. Provisional Patent Application Ser. No. 61/955,554 filed Mar. 19, 2014, the entire disclosures of which are incorporated by reference herein.

The present invention relates to a process for preparing compound 1 or 1a that is useful as an antifungal agent. In particular, the invention seeks to provide a new methodology for preparing compound 1 or 1a and substituted derivatives thereof.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymnes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof. Similarly, methods of synthesizing such therapeutic agents on the laboratory and, ultimately, commercial scale is needed. Addition of metal-based nucleophiles (Zn, Zr, Ce, Ti, Mg, Mn, Li) to azole-methyl substituted ketones have been effected in the synthesis of voriconazole (M. Butters, *Org. Process Res. Dev.* 2001, 5, 28-36). The nucleophile in these examples was an ethylpyrimidine substrate. Similarly, optically active azole-methyl epoxide has been prepared as precursor electrophile toward the synthesis of ravuconazole (A. Tsurumoka, *Chem. Pharm. Bull.* 1998, 46, 623-630). Despite this, the development of methodology with improved efficiency and selectivity is desirable.

BRIEF SUMMARY OF THE INVENTION

The invention is directed toward a compound of any of the formulae herein (e.g., Formula 1 or 1a), and methods of synthesis of a compound of any of the formulae herein (e.g., Formula 1 or 1a). The methods can comprise the compounds herein. A first aspect of the invention relates to a process for preparing a compound of formula 1 or 1a, or a pharmaceutically acceptable salt, hydrate, solvate, complex or prodrug thereof.

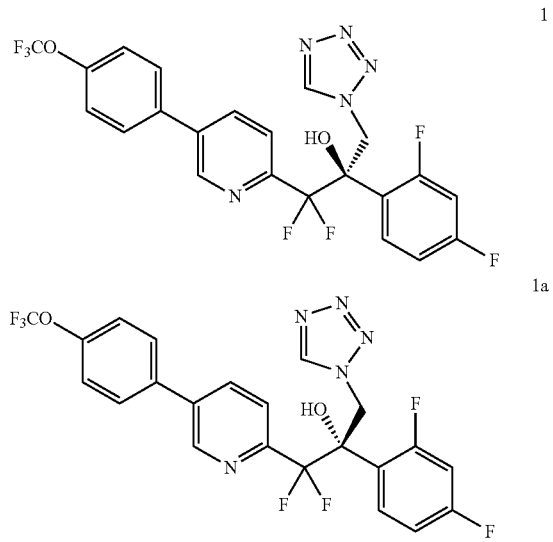

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions.

Methods for assessing metal-ligand binding interactions are known in the art as exemplified in references including, for example, "Principles of Bioinorganic Chemistry" by Lippard and Berg, University Science Books, (1994): "Mechanisms of Inorganic Reactions" by Basolo and Pearson John Wiley & Sons Inc: 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In certain instances, the compounds of the invention are selected from the following of Formula 1 or 1a (and pharmaceutically acceptable salts, solvates, or hydrates thereof):

2-(2,4-Difluorophenyl)-1,1-difluoro-3-(1H-tetrazol-1-yl)-1-(5-(4-(trifluoromethoxy)phenyl)pyridin-2-yl) propan-2-ol (1 or 1a).

In the following aspects, reference is made to the schemes and compounds herein, including the reagents and reaction conditions delineated herein. Other aspects include any of the compounds, reagents, transformations or methods thereof delineated in the examples herein (in whole or in part), including as embodiments with single elements (e.g., compounds or transformations) or embodiments including multiple elements (e.g., compounds or transformations).

In one aspect, the invention provides a process to prepare compound of formula 6:

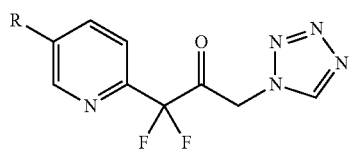

comprising decarboxylating a compound of formula 5:

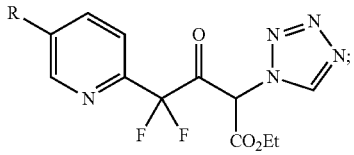

to compound 6;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare ketone 8:

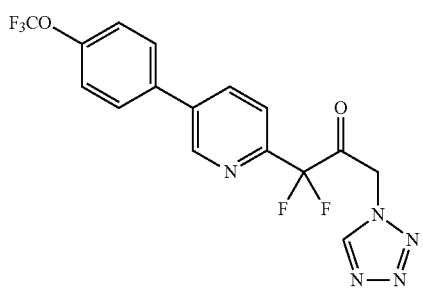

comprising arylating a compound of formula 6:

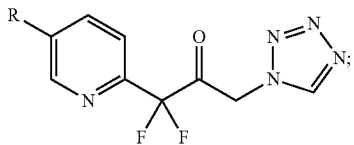

to ketone 8;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a synthetic process to prepare a compound of formula 15:

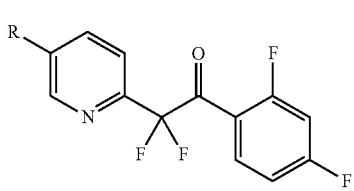

comprising forming a ketone of a compound of formula 3:

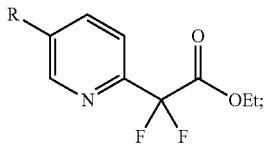

to provide a compound of formula 15;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare compound 1 or 1a, or a mixture thereof:

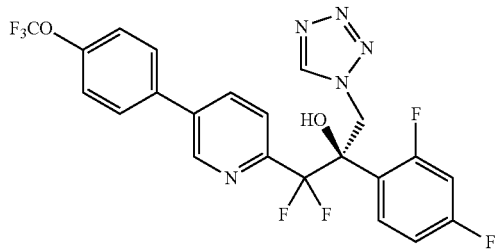

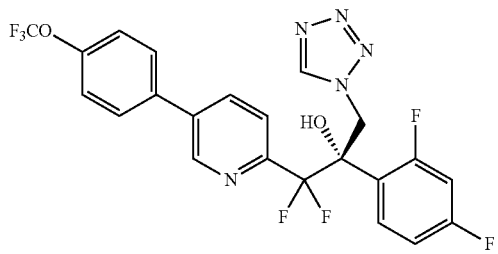

comprising arylating ketone 8:

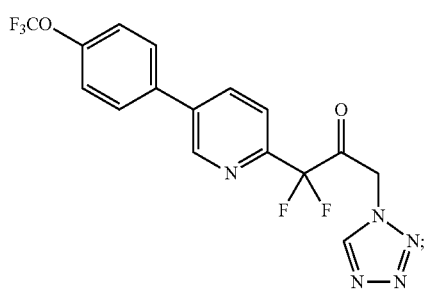

to provide compound 1 or 1a, or a mixture thereof.

In one embodiment, the invention provides a process comprising reacting ketone 8:

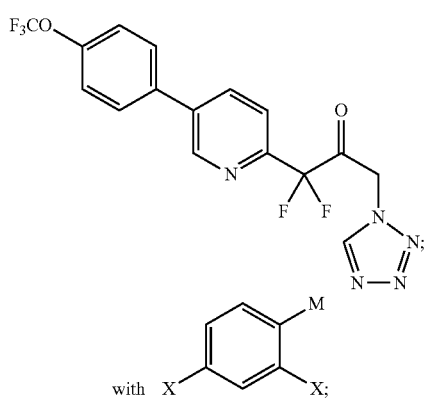

with 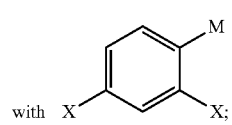

wherein M is Mg, MgX, Zn, or Ce; and X is halogen; to provide compound 1 or 1a, or a mixture thereof:

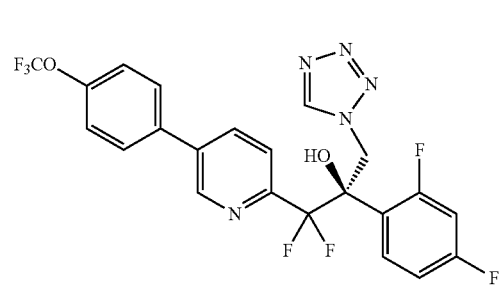

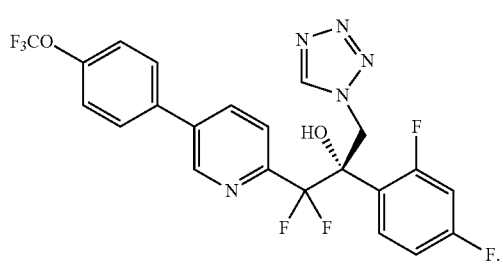

In another embodiment, the invention provides a process further comprising arylating a compound of formula 6:

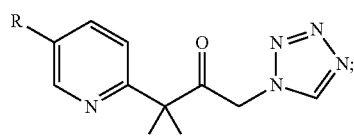

to provide ketone 8:

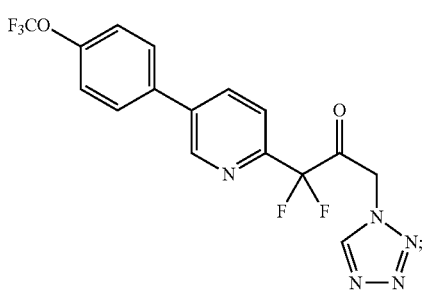

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In certain embodiments, the invention provides a process comprising reacting a compound of formula 6:

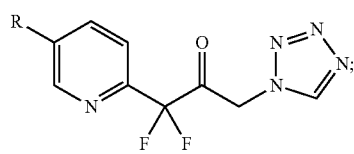

to provide ketone 8:

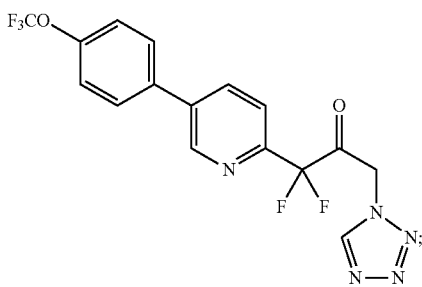

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In certain embodiments, the invention provides a process comprising reacting a compound of formula 6:

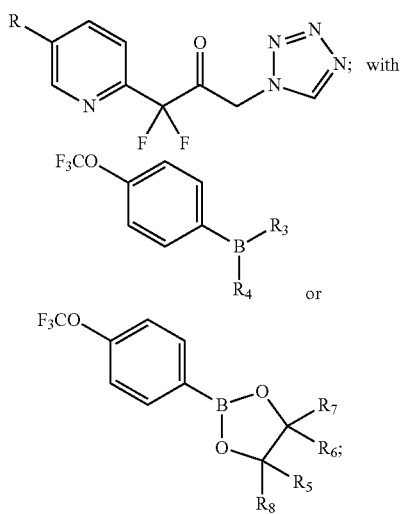

to provide ketone 8:

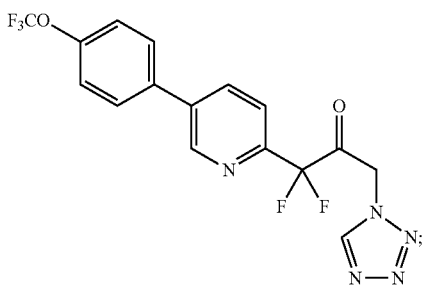

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl;

each $R_3$ and $R_4$ are each independently alkyl, substituted alkyl, aryl, substituted aryl, alkoxy, substituted alkoxy, OH, aryloxy, or substituted aryloxy; and each $R_5$, $R_6$, $R_7$, and $R_8$ are each independently H, alkyl, substituted alkyl, aryl, substituted aryl, alkoxy, substituted alkoxy, aryloxy, or substituted aryloxy.

In another aspect, the invention provides a synthetic process to prepare compound 1 or 1a, or a mixture thereof:

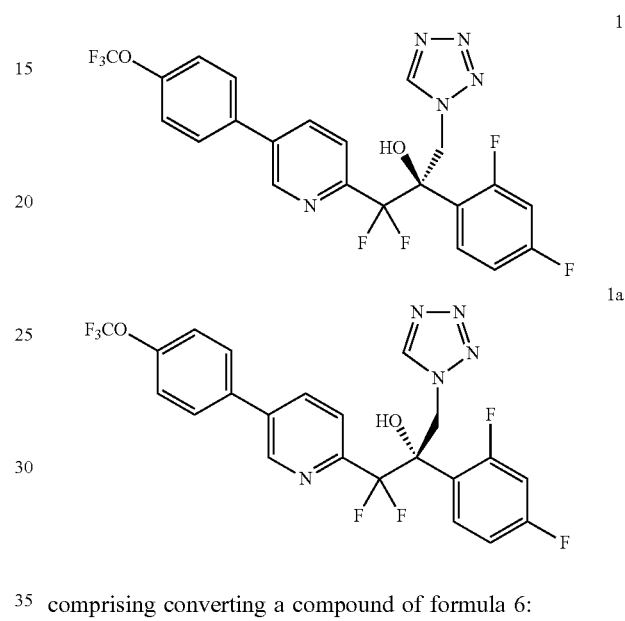

comprising converting a compound of formula 6:

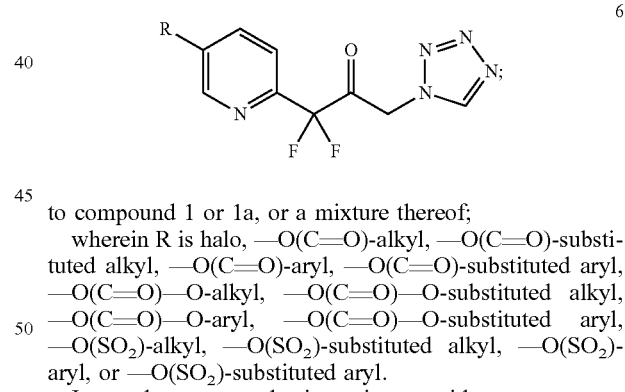

to compound 1 or 1a, or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, the invention provides a process to prepare compound 1 or 1a, or a mixture thereof:

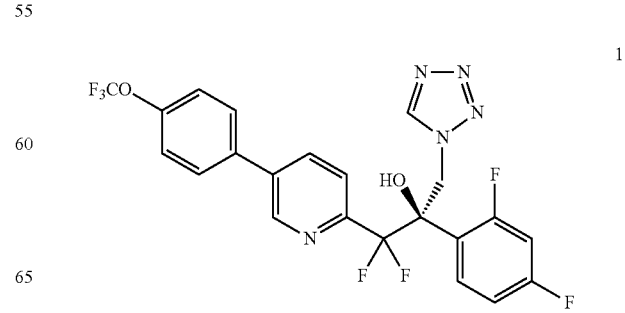

-continued

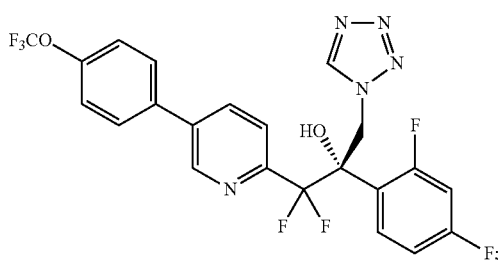
1a comprising converting a compound of formula 9 or 9a, or a mixture thereof:

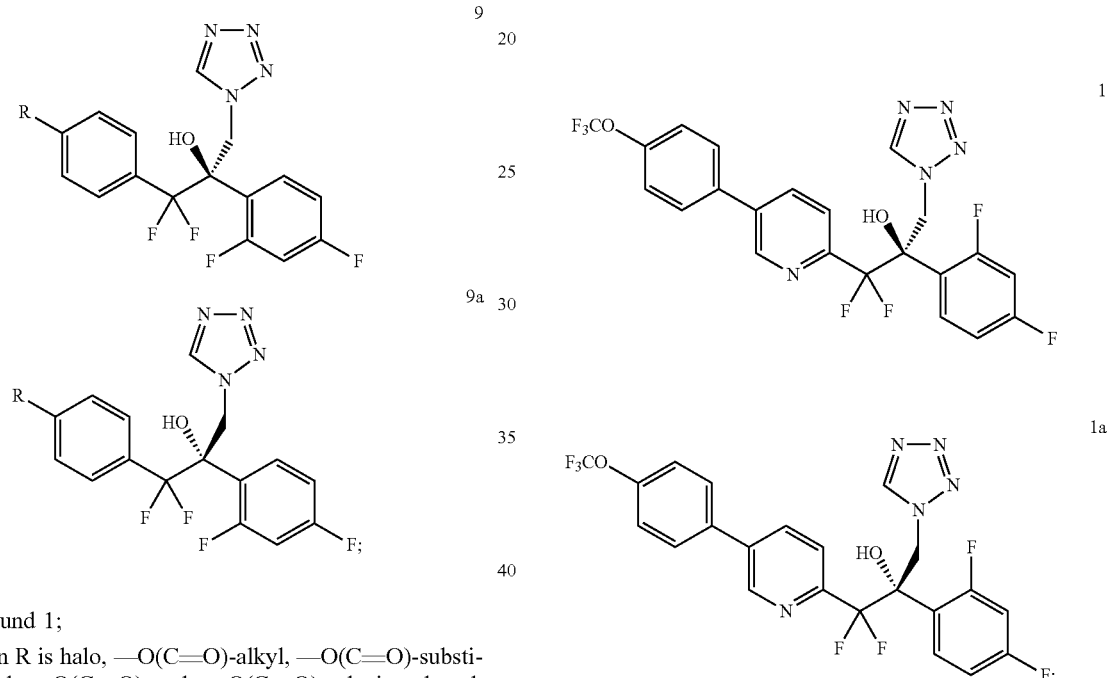

to compound 1;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, the invention provides a process to prepare ketone 8:

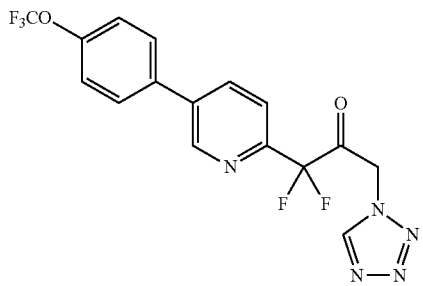

comprising converting difluoropyridine 12:

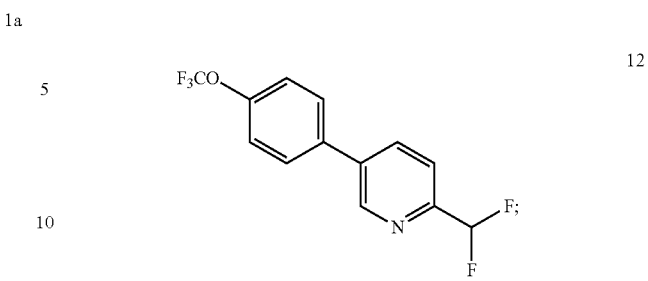

to compound 8.

In another aspect, the invention provides a synthetic process to prepare compound 1 or 1a, or a mixture thereof:

comprising converting a compound of formula 15:

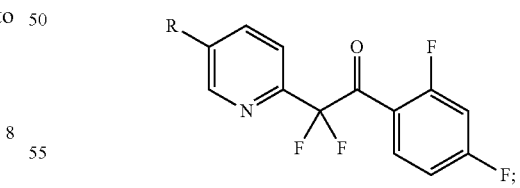

to compound 1 or 1a, or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, the invention provides a synthetic process to prepare compound 1 or 1a, or a mixture thereof:

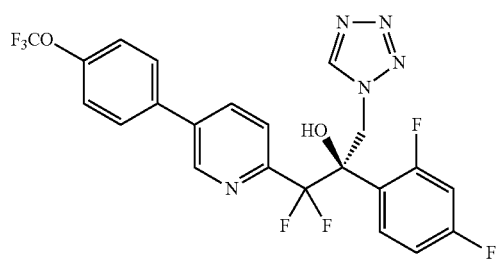

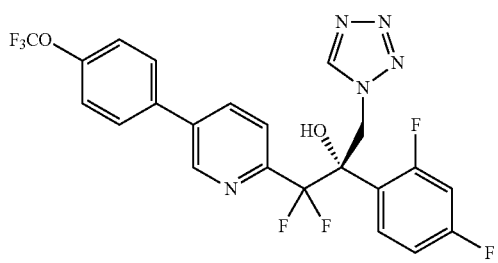

comprising converting a compound of formula 19 or 19a, or a mixture thereof:

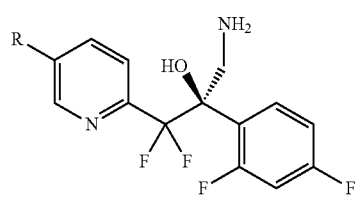

19

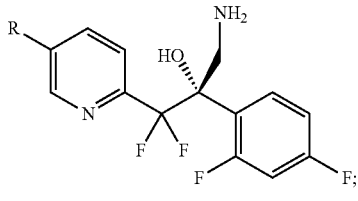

19a to compound 1 or 1a, or a mixture thereof;
wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO₂)-alkyl, —O(SO₂)-substituted alkyl, —O(SO₂)-aryl, or —O(SO₂)-substituted aryl.

In another aspect, the invention provides a synthetic process to prepare compound 1 or 1a, or a mixture thereof:

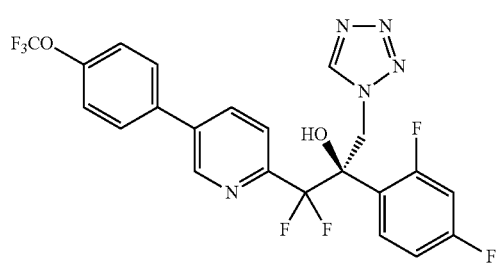

1

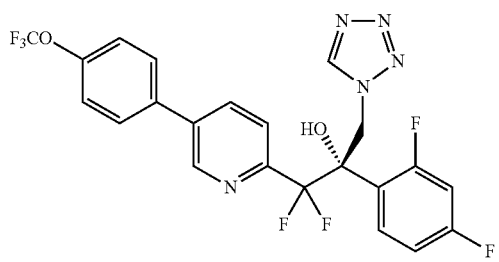

1a comprising converting a compound of formula 20 or 20a, or a mixture thereof:

20

20a to compound 1 or 1a, or a mixture thereof;
wherein R₂ is

In another aspect, the invention provides a process to prepare compound 1 or 1a, or a mixture thereof:

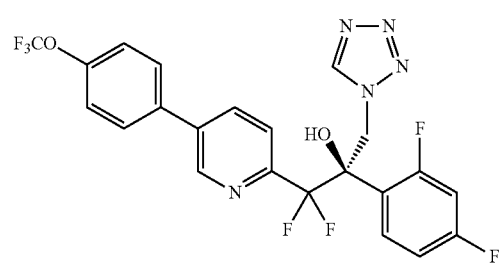

1

-continued

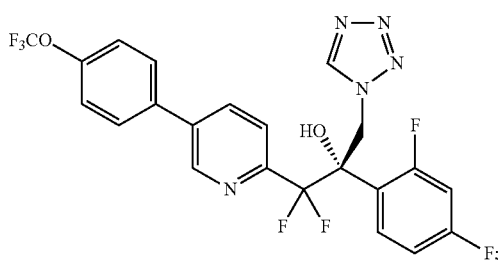

comprising converting a compound of formula 23 or 23a, or a mixture thereof:

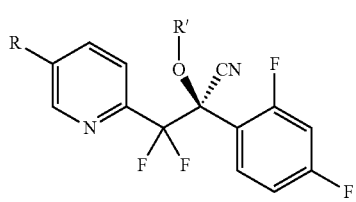

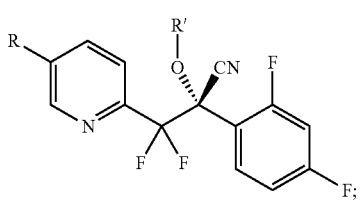

to compound 1 or 1a, or a mixture thereof;

wherein R is halo, —O(C═O)-alkyl, —O(C═O)-substituted alkyl, —O(C═O)-aryl, —O(C═O)-substituted aryl, —O((C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl; and R' is trimethylsilyl or H.

In another aspect, the invention provides a process to prepare compound 1 or 1a, or a mixture thereof:

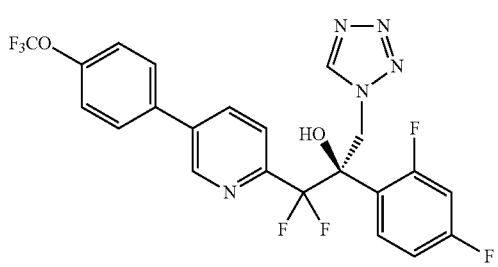

-continued

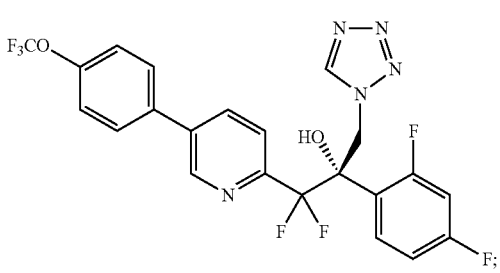

comprising converting a compound of formula 24 or 24a, or a mixture thereof:

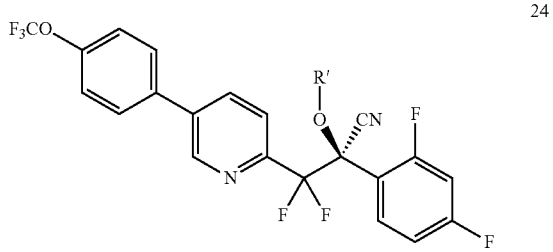

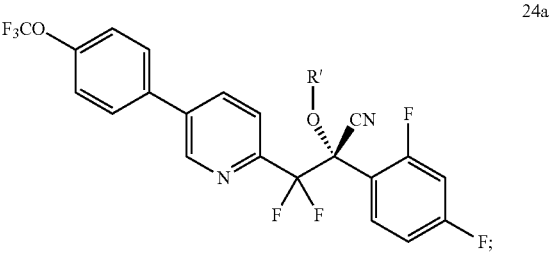

to compound 1 or 1a, or a mixture thereof;

wherein R' is trimethylsilyl or H.

In another aspect, the invention provides a process to prepare compound 1 or 1a, or a mixture thereof:

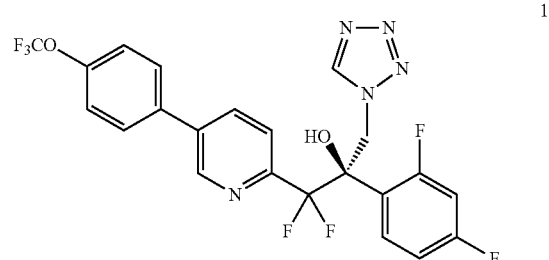

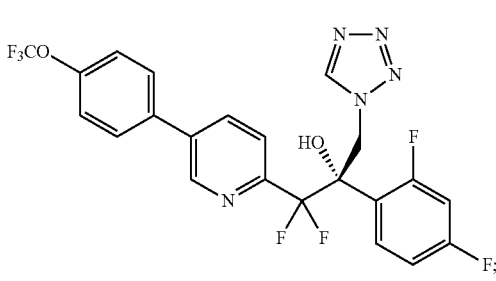

i. nitromethylating a compound of formula 15,
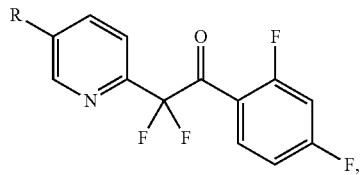
to provide a compound of formula 17 or 17a,
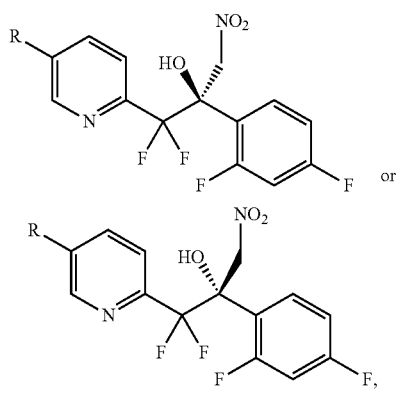
or a mixture thereof;
ii. reducing a compound of formula 17 or 17a,
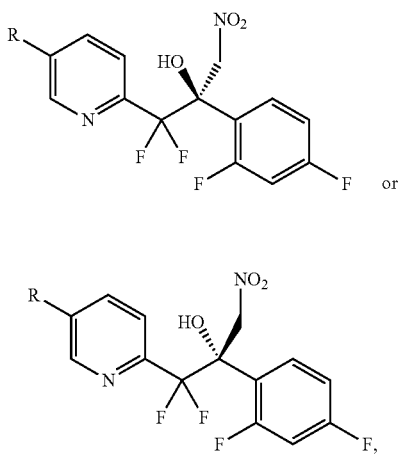
or a mixture thereof, to provide a compound of formula 19 or 19a,
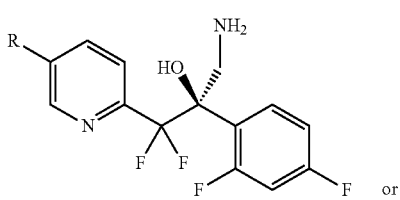
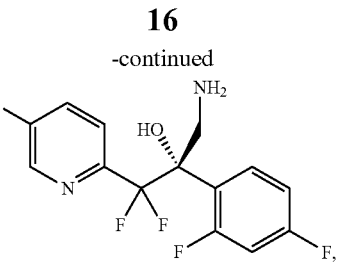
or a mixture thereof;
iii. forming the tetrazole of a compound of formula 19 or 19a.
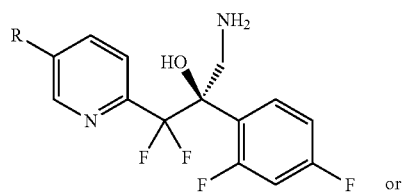
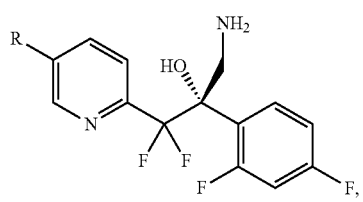
or a mixture thereof, to provide a compound of formula 9 or 9a,
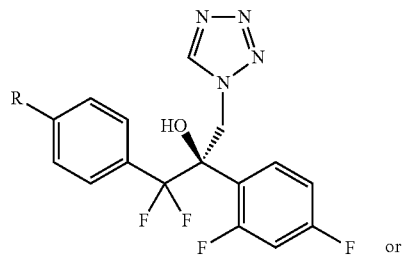
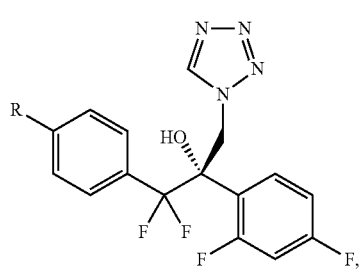
or a mixture thereof; and iv. arylating a compound of formula 9 or 9a,

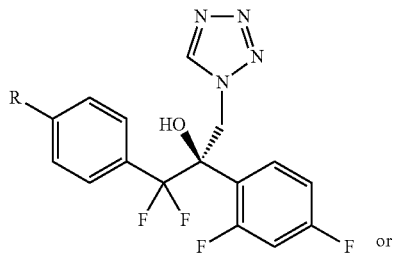

or

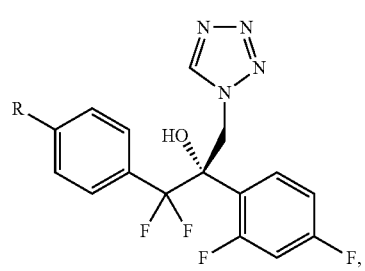

or a mixture thereof, to provide compound 1 or 1a,

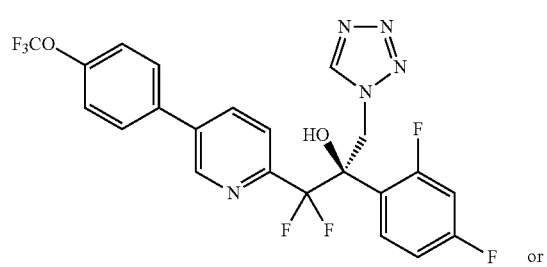

or

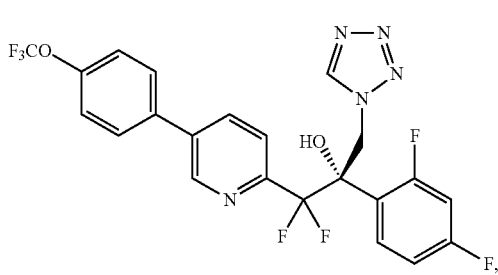

or a mixture thereof;

wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO₂)-alkyl, —O(SO₂)-substituted alkyl, —O(SO₂)-aryl, or —O(SO₂)-substituted aryl.

In another aspect, the invention provides a synthetic process to prepare compound 1 or 1a, or a mixture thereof comprising:

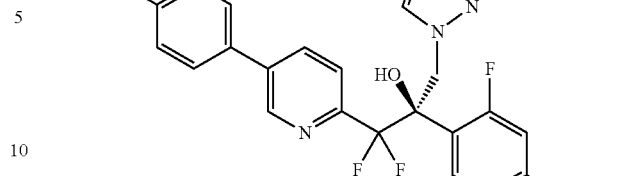

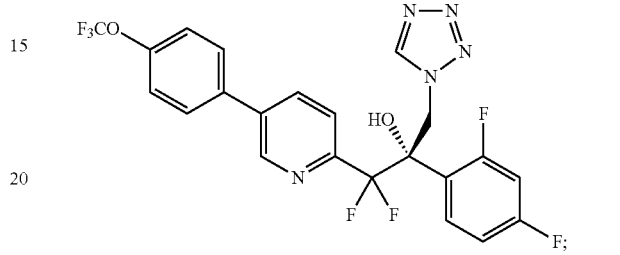

i. arylating a compound of formula 15,

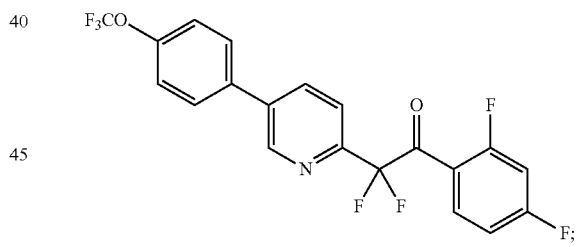

to provide ketone 16,

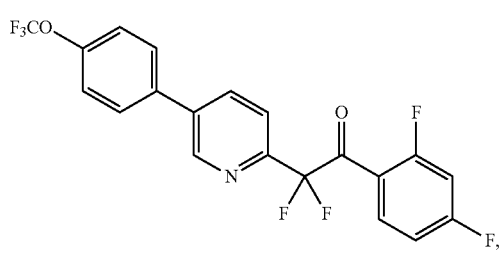 [SMILES: O=C(c1ccc(F)cc1F)C(F)(F)c1ccc(-c2ccc(OC(F)(F)F)cc2)cn1]

ii. nitromethylating ketone 16, to provide nitro-alcohol 18 or 18a,

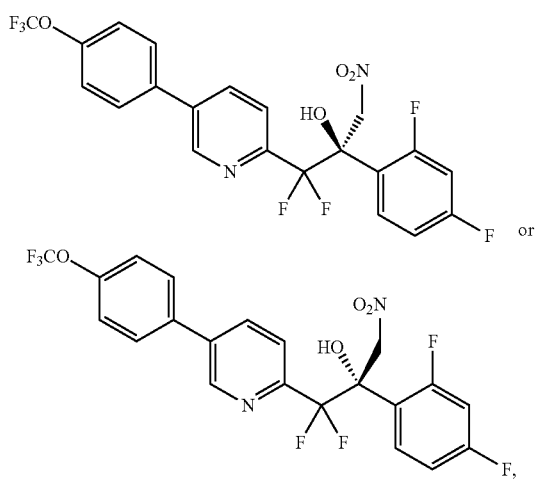

or a mixture thereof;
iii. reducing nitro-alcohol 18 or 18a,

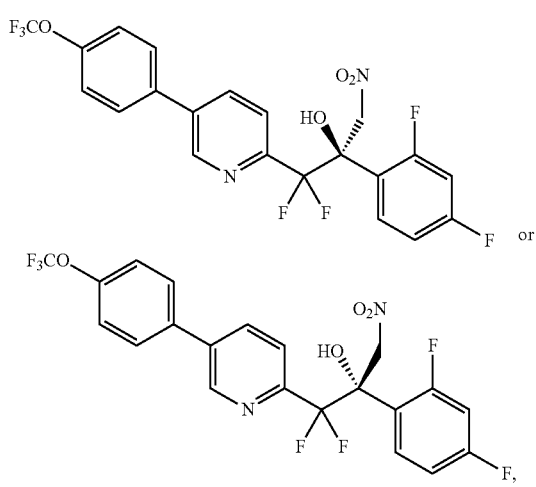

or a mixture thereof, to provide amino-alcohol 20 or 20a,

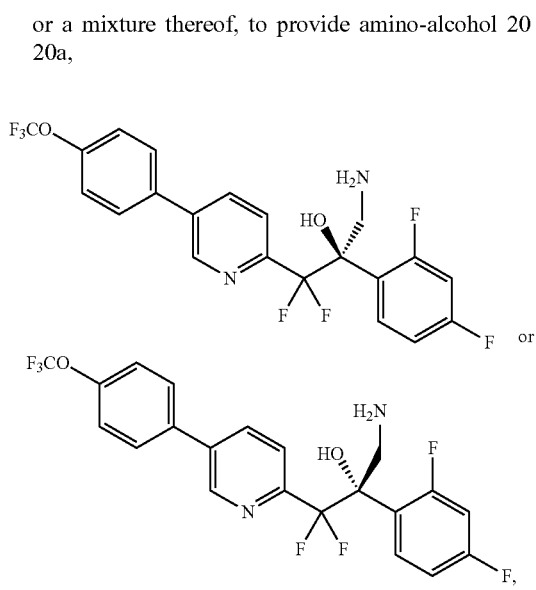

or a mixture thereof; and
iv. forming the tetrazole of amino-alcohol 20 or 20a,

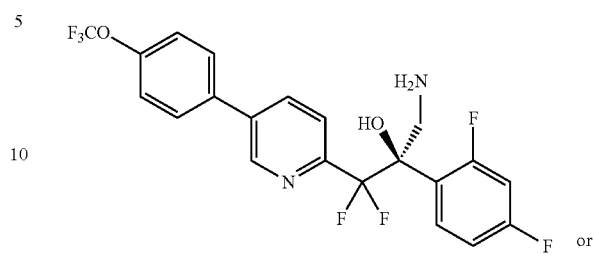

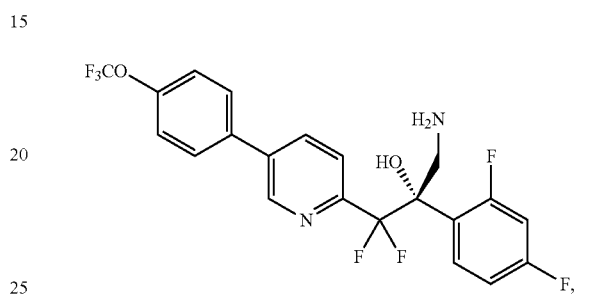

or a mixture thereof, to provide compound 1 or 1a,

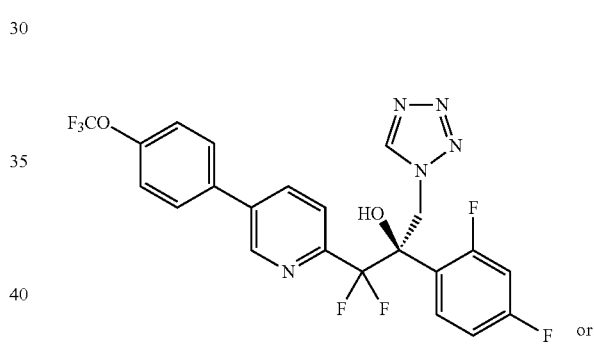

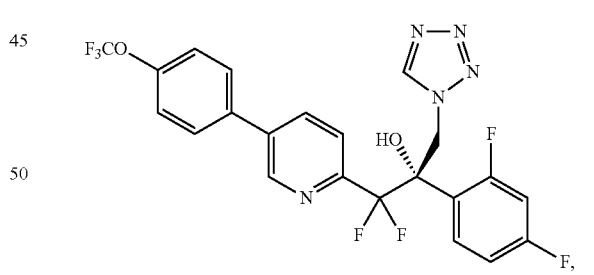

or a mixture thereof;
wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a synthetic process to prepare compound 1 or 1a, or a mixture thereof comprising:

1
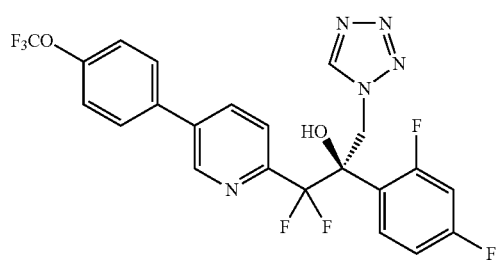
1a
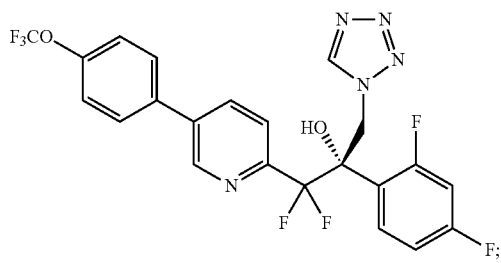
i. nitromethylating a compound of formula 15,
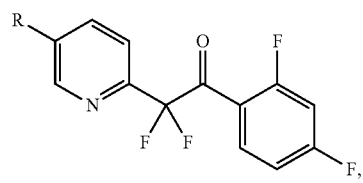
to provide a compound of formula 17 or 17a,
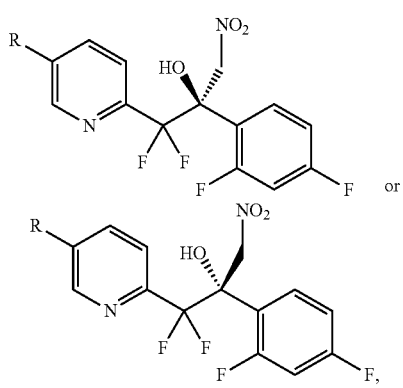
or a mixture thereof;
ii. arylating a compound of formula 17 or 17a,
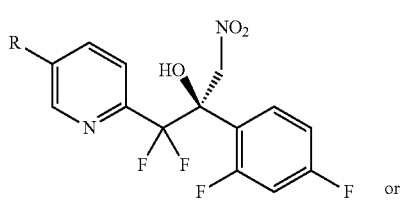
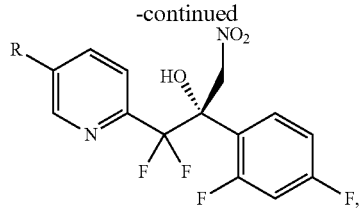
or a mixture thereof, to provide nitro-alcohol 18 or 18a,
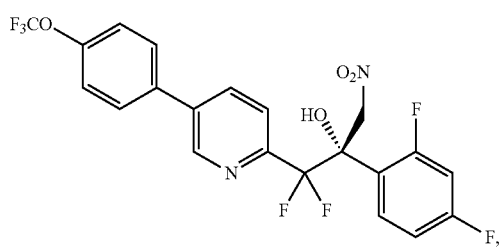
or a mixture thereof;
iii. reducing nitro-alcohol 18 or 18a,
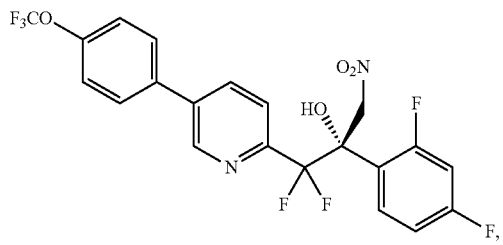
or a mixture thereof, to provide amino-alcohol 20 or 20a,

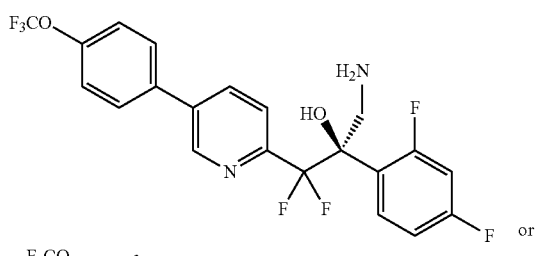

or

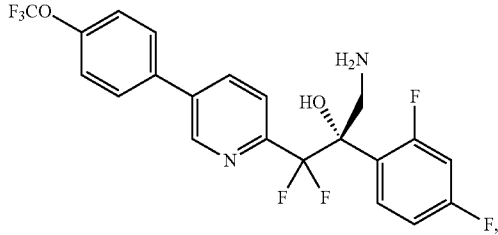

or a mixture thereof; and
iv. forming the tetrazole of amino-alcohol 20 or 20a,

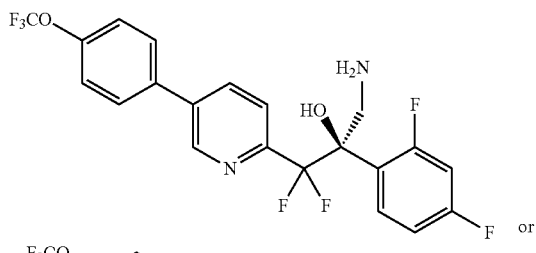

or

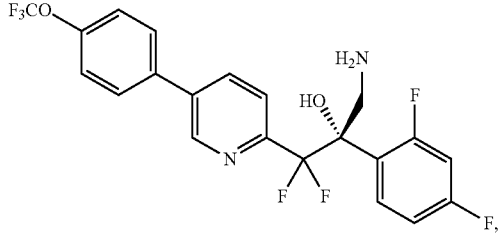

or a mixture thereof, to provide compound 1 or 1a,

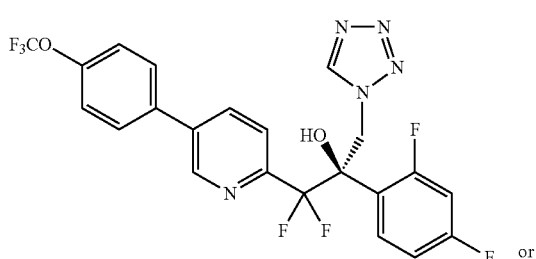

or

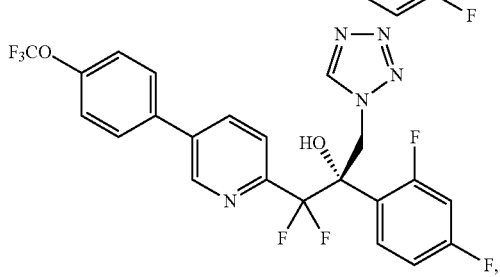

or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, the invention provides a synthetic process to prepare compound 1 or 1a, or a mixture thereof comprising:

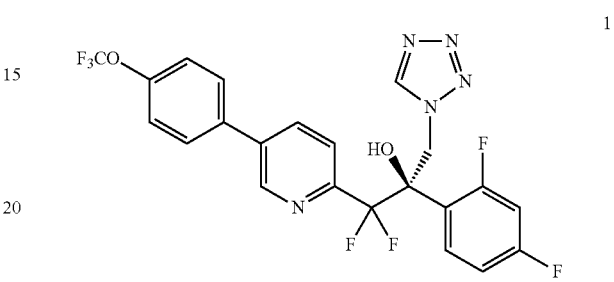

1

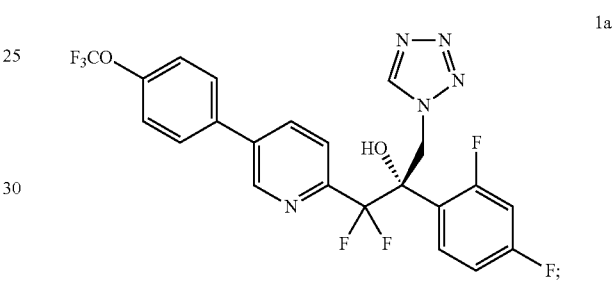

1a i. nitromethylating a compound of formula 15,

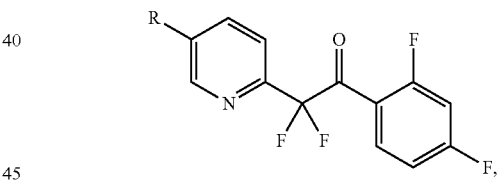

to provide a compound of formula 17 or 17a,

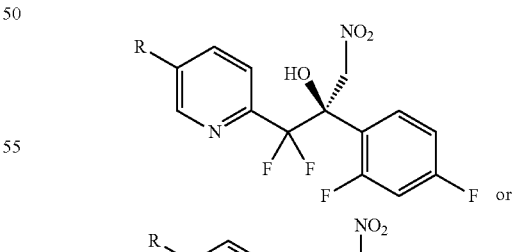

or

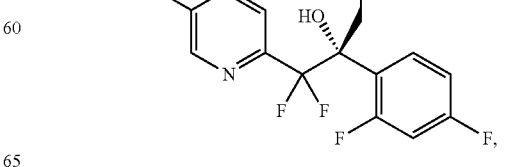

or a mixture thereof;

ii. reducing a compound of formula 17 or 17a,
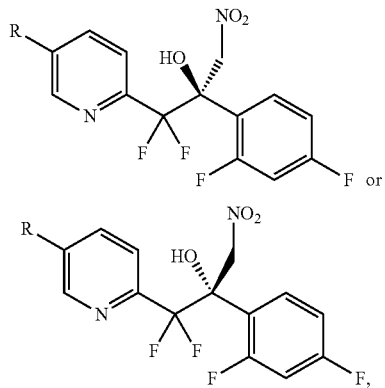
or a mixture thereof, to provide a compound of formula 19 or 19a,
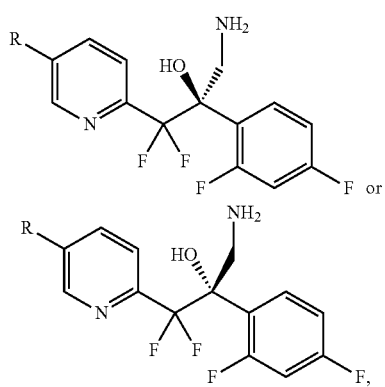
or a mixture thereof;
iii. arylating a compound of formula 19 or 19a,
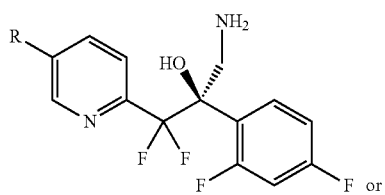
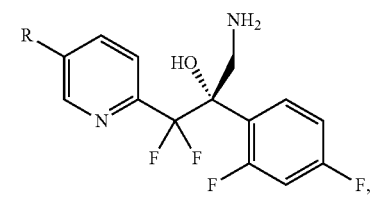
or a mixture thereof, to provide amino-alcohol 20 or 20a,
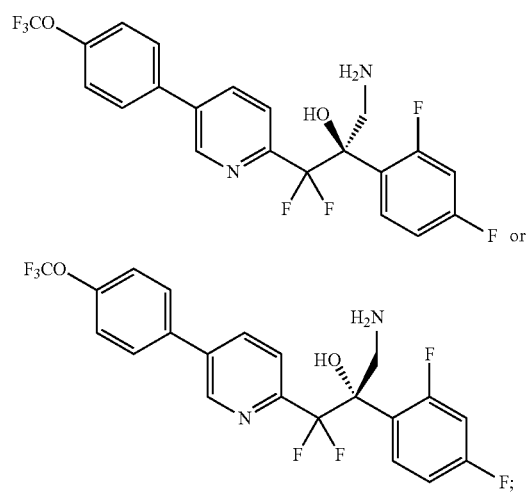
and
iv. forming the tetrazole of amino-alcohol 20 or 20a,
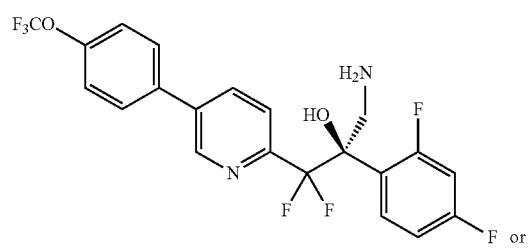
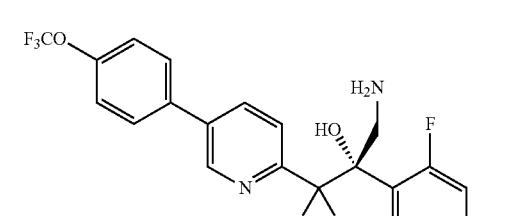
or a mixture thereof, to provide compound 1 or 1a,
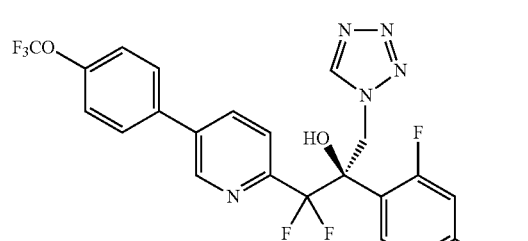

-continued

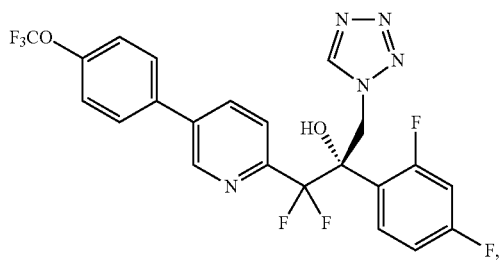

or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a synthetic process to prepare a compound of formula 23 or 23a, or a mixture thereof:

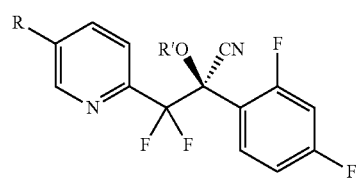

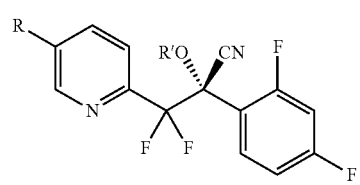

comprising cyanation of a compound of formula 15:

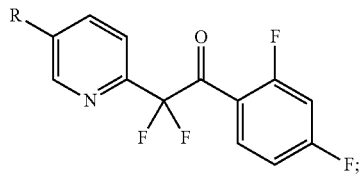

to compound 23 or 23a, or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl; and R' is H or TMS.

In another aspect, the invention provides a synthetic process to prepare a compound of formula 19 or 19a, or a mixture thereof:

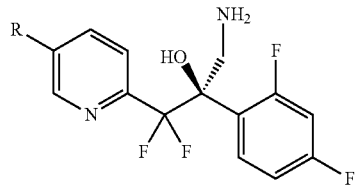

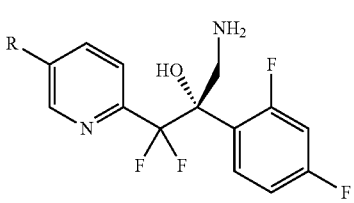

comprising reduction of a compound of formula 23 or 23a, or a mixture thereof:

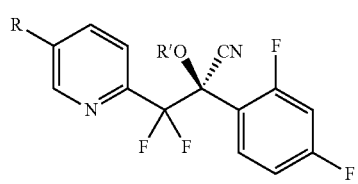

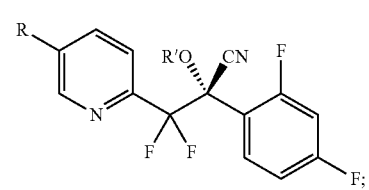

to compound 19;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl; and R' is H or TMS.

In another aspect, the invention provides a synthetic process to prepare compound 1 or 1a, or a mixture thereof comprising:

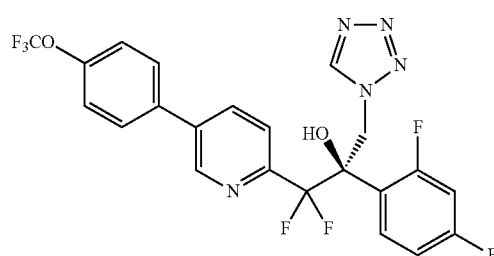

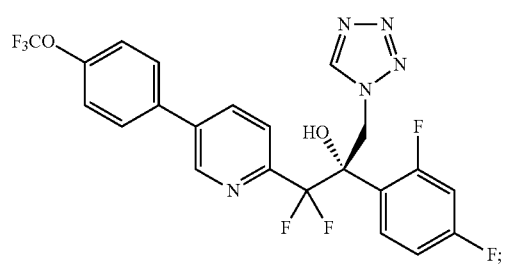
i. arylating a compound of formula 15,
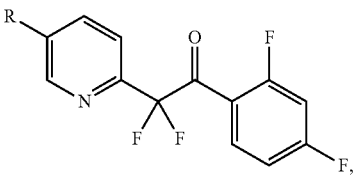
to provide ketone 16,
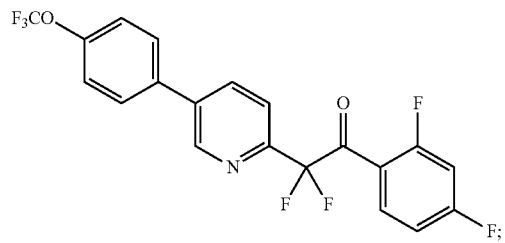
ii. forming the cyanohydrin of ketone 16,
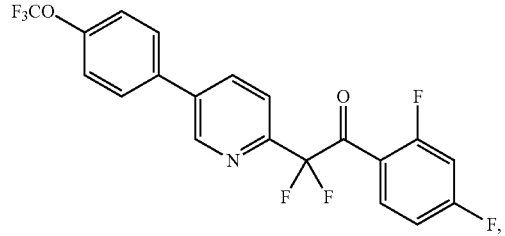 [SMILES: O=C(c1ccc(F)cc1F)C(F)(F)c1ccc(-c2ccc(OC(F)(F)F)cc2)cn1]
to provide nitrile 24 or 24a,
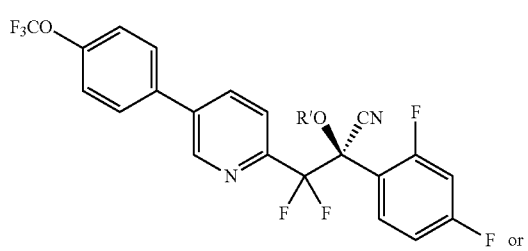
or a mixture thereof;
iii. reducing nitrile 24 or 24a,
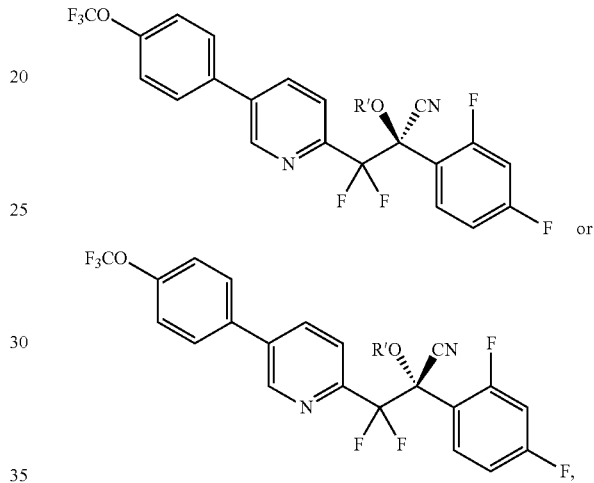
or a mixture thereof, to provide amino-alcohol 20 or 20a,
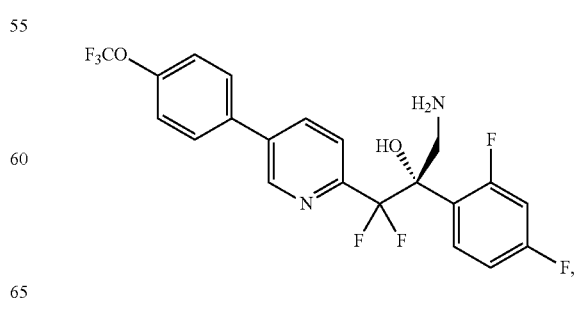
or a mixture thereof; and iv. forming the tetrazole of amino-alcohol 20 or 20a,

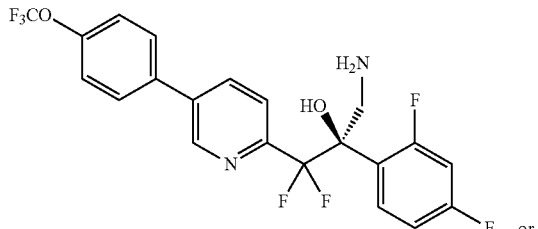

or

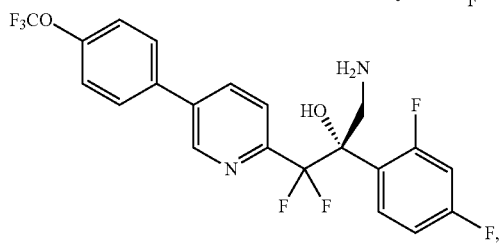

or a mixture thereof, to provide compound 1 or 1a,

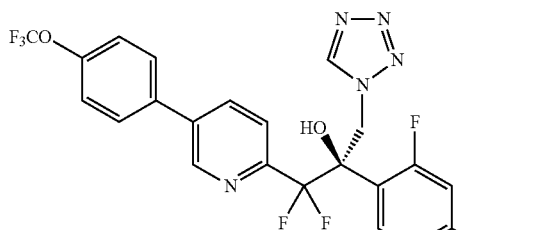

or

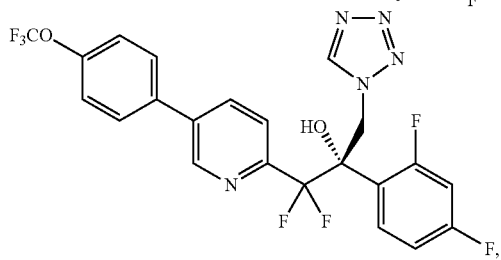

or a mixture thereof;
wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl; and
R' is H or TMS.

In another aspect, the invention provides a synthetic process to prepare compound 1 or 1a, or a mixture thereof comprising:

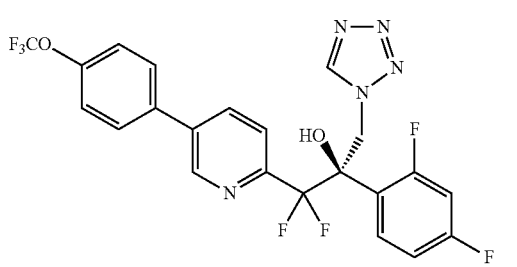

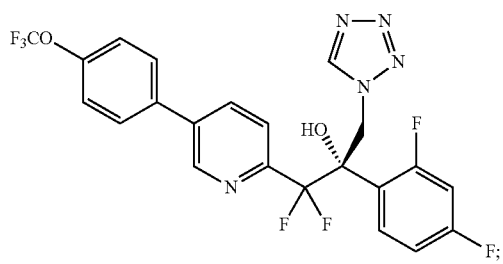

i. cyanating a compound of formula 15,

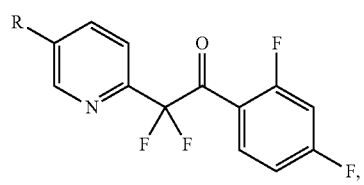

to provide a compound of formula 23 or 23a

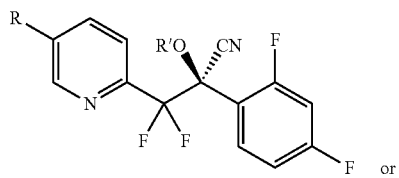

or

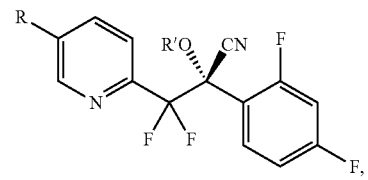

or a mixture thereof;

ii. arylating a compound of formula 23 or 23a,

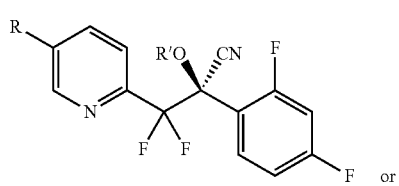

or

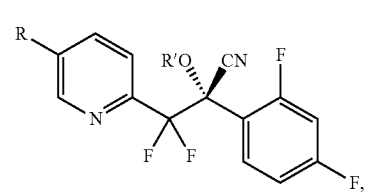

or a mixture thereof, to provide nitrile 24 or 24a,

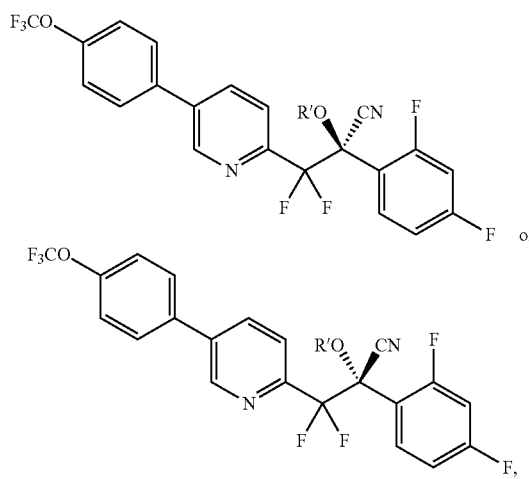

or a mixture thereof;
iii. reducing nitrile 24 or 24a,

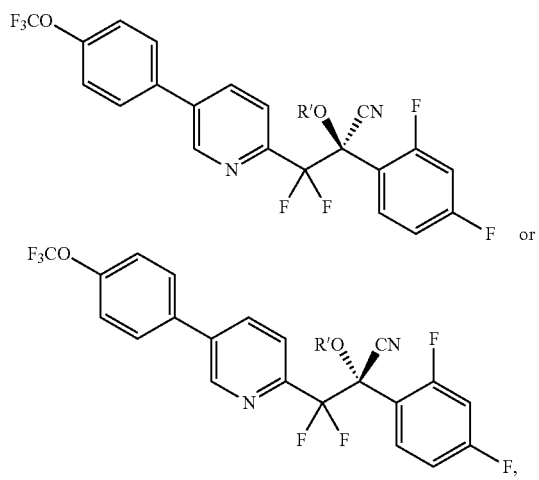

or a mixture thereof, to provide amino-alcohol 20 or 20a,

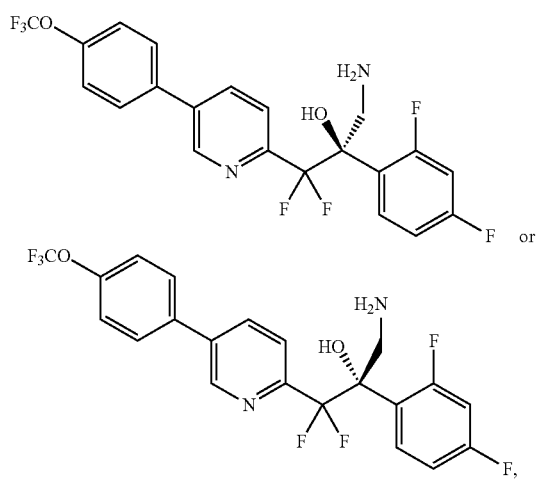

or a mixture thereof; and iv. forming the tetrazole of amino-alcohol 20 or 20a,

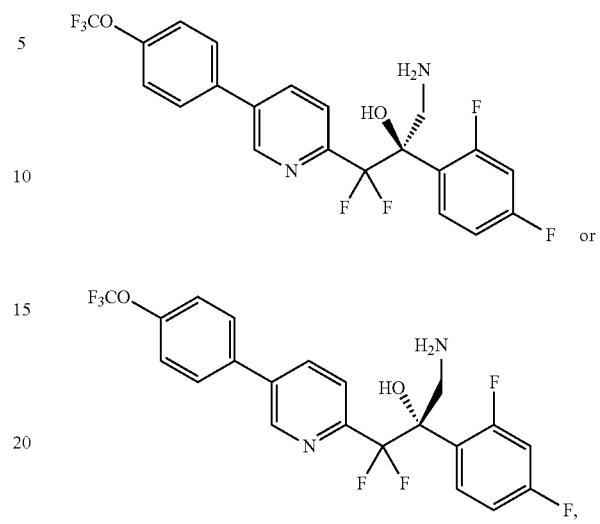

or a mixture thereof, to provide compound 1 or 1a,

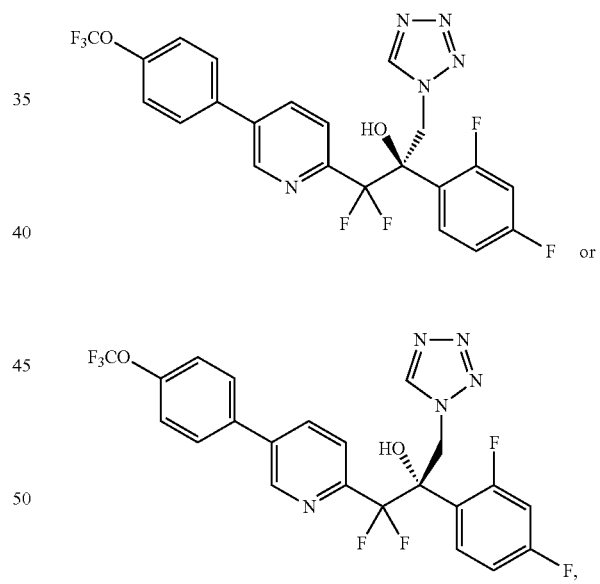

or a mixture thereof;
wherein R is halo, —(C=O)-alkyl, —(O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl; and
R' is H or TMS.

In another aspect, the invention provides a synthetic process to prepare compound 1 or 1a, or a mixture thereof comprising:

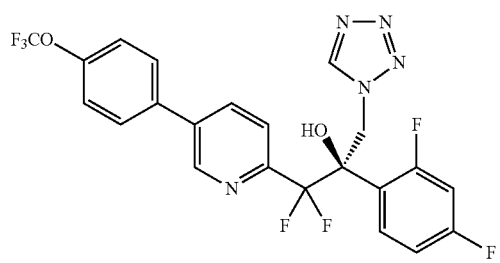
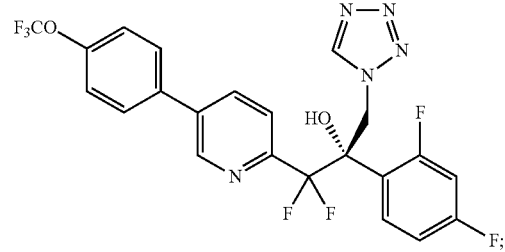
i. cyanating a compound of formula 15,
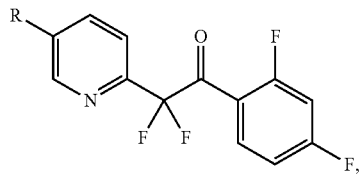
to provide a compound of formula 23 or 23a,
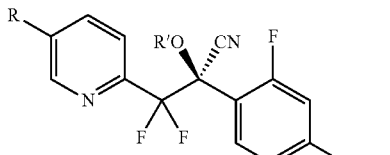
or a mixture thereof;
ii. reducing a compound of formula 23 or 23a,
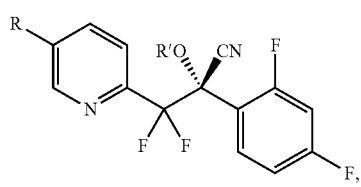
or
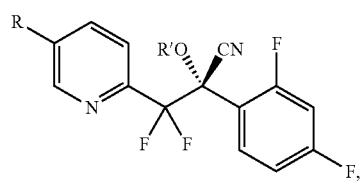
or a mixture thereof, to provide a compound of formula 19 or 19a,
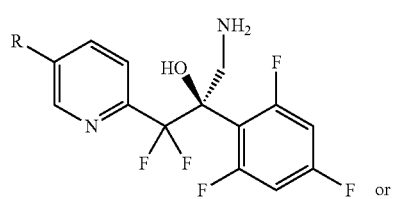
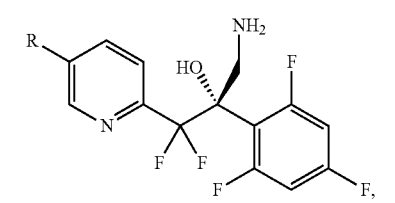
or a mixture thereof;
iii. arylating a compound of formula 19 or 19a,
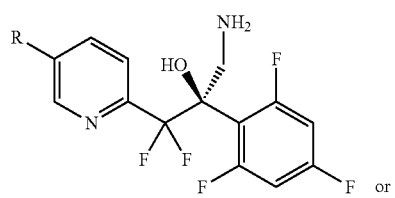
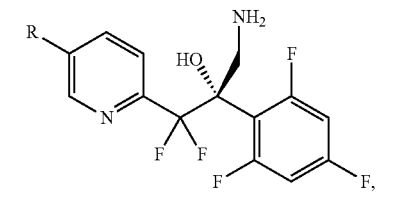
or a mixture thereof, to provide amino-alcohol 20 or 20a,
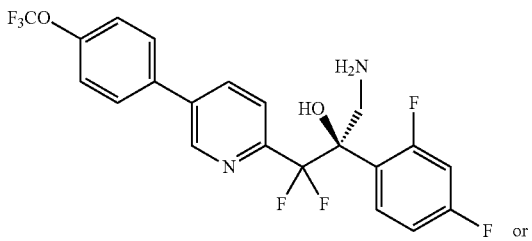

-continued

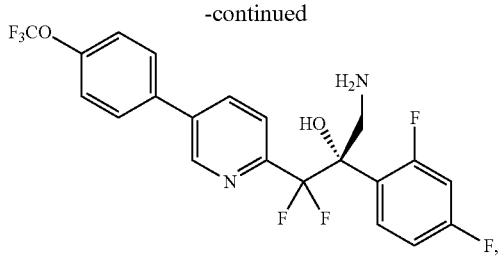

or a mixture thereof;
iv. forming the tetrazole of amino-alcohol 20 or 20a,

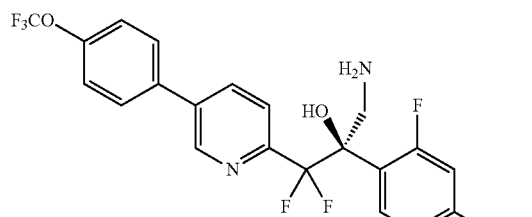

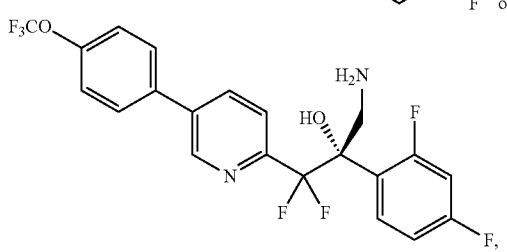

or a mixture thereof, to provide compound 1 or 1a,

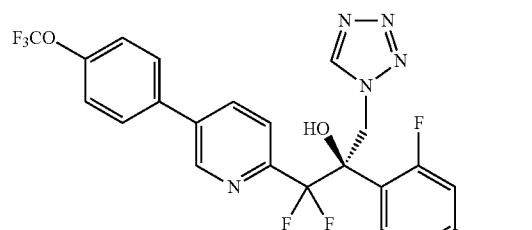

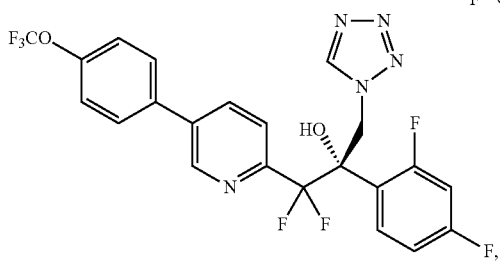

or a mixture thereof;
wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl; and
R' is H or TMS.

In another aspect, the invention provides a synthetic process to prepare compound 1 or 1a, or a mixture thereof comprising:

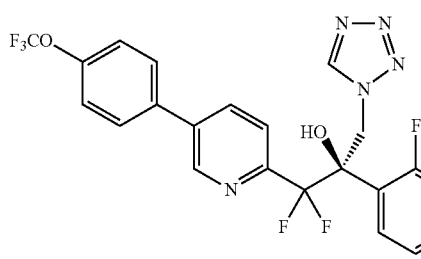

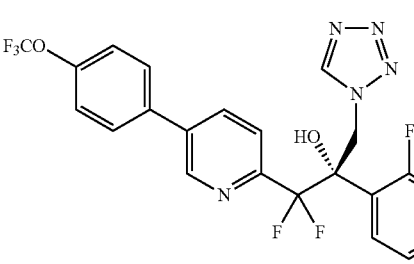

i. cyanating a compound of formula 15,

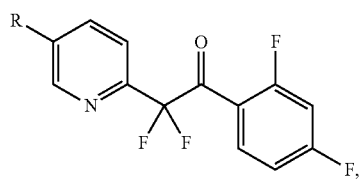

to provide a compound of formula 23 or 23a,

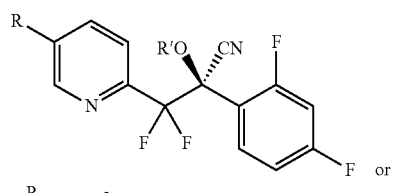

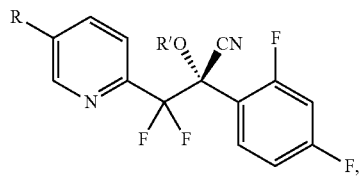

or a mixture thereof;
ii. reducing a compound of formula 23 or 23a,

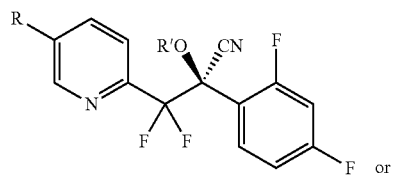

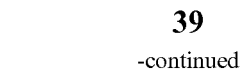

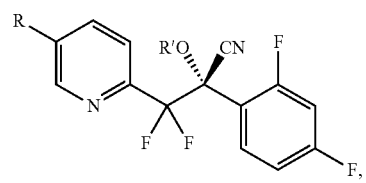

or a mixture thereof, to provide a compound of formula 19 or 19a,

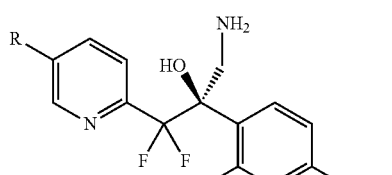

or a mixture thereof;

iii. forming the tetrazole of a compound of formula 19 or 19a,

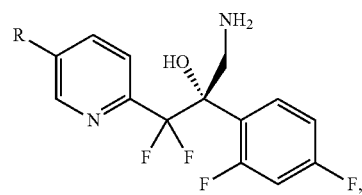

or a mixture thereof, to provide a compound of formula 9 or 9a,

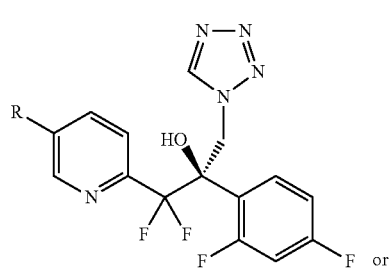

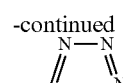

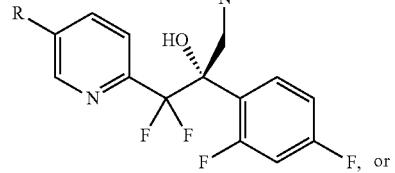

or a mixture thereof;

iv. forming the tetrazole of a compound of formula 9 or 9a,

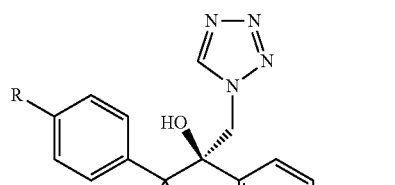

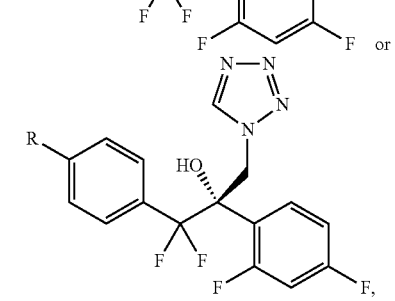

or a mixture thereof, to provide compound 1 or 1a,

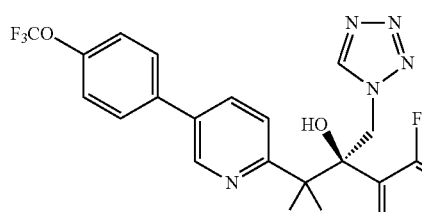

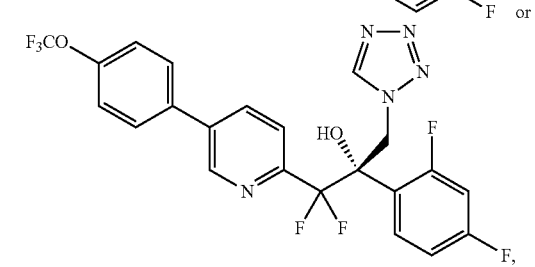

or a mixture thereof;

wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO₂)-alkyl, —O(SO₂)-substituted alkyl, —O(SO₂)-aryl, or —O(SO₂)-substituted aryl; and R' is H or TMS.

In another aspect, the invention provides a synthetic process to prepare compound 1 or 1a, or a mixture thereof comprising:

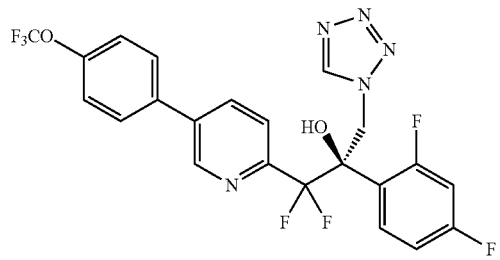

1

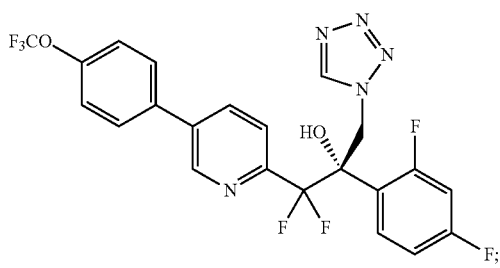

1a i. arylating a compound of formula 19 or 19a,

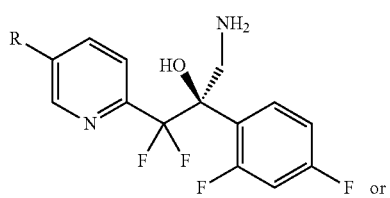

or

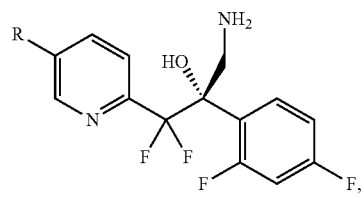

or a mixture thereof, to provide amino-alcohol 20 or 20a,

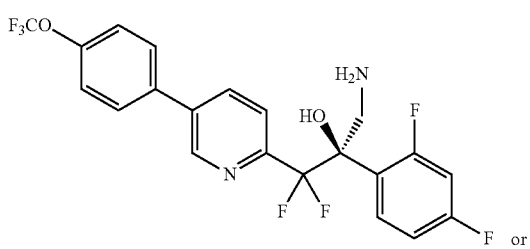

or

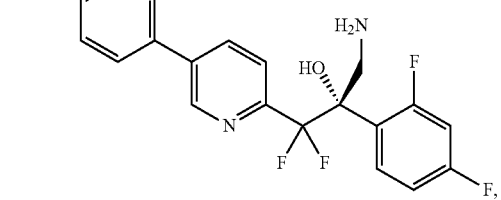

or a mixture thereof; and ii. forming the tetrazole of amino-alcohol 20 or 20a,

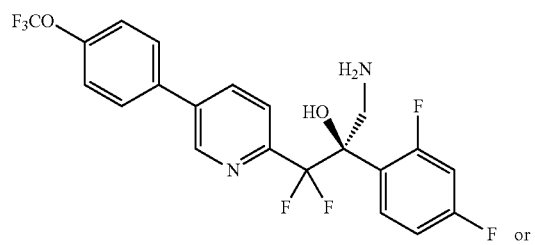

or a mixture thereof, to provide compound 1 or 1a,

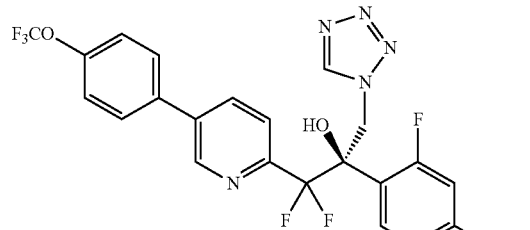

or

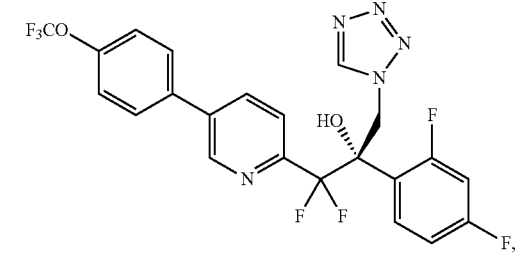

or a mixture thereof;

wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a synthetic process to prepare compound 1 or 1a, or a mixture thereof comprising:

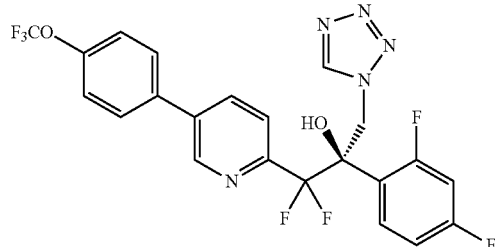

1

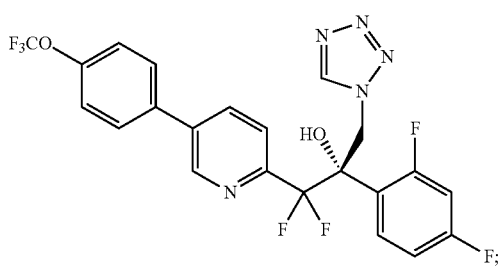

1a;

i. forming the tetrazole of a compound of formula 19 or 19a,

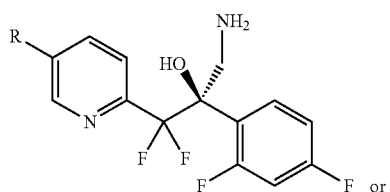

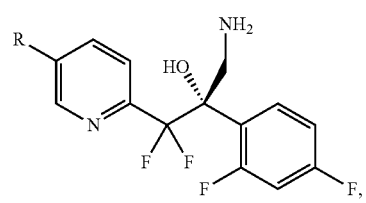

or a mixture thereof, to provide amino-alcohol 9 or 9a,

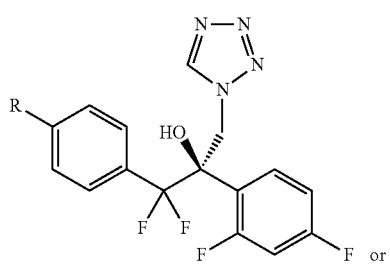

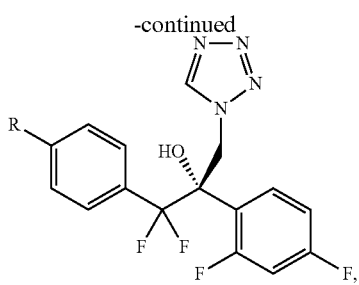

or a mixture thereof; and
ii. arylating amino-alcohol 9 or 9,

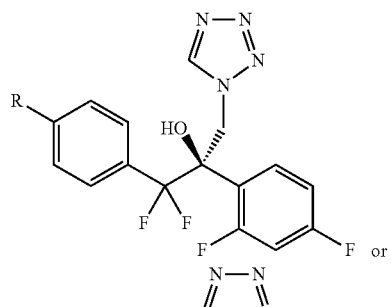

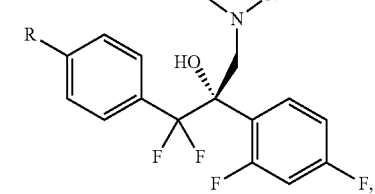

or a mixture thereof, to provide compound 1 or 1a,

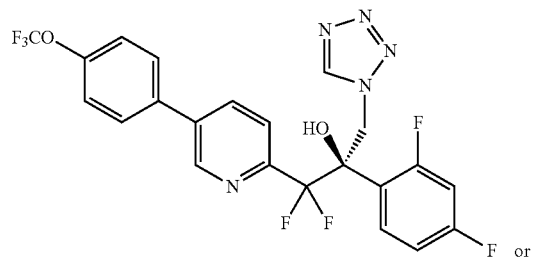

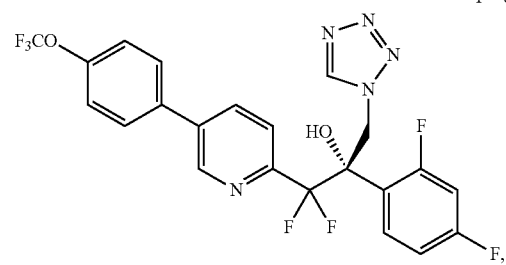

or a mixture thereof;
wherein R is halo, —O(C=O)-alkyl. —(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, the invention provides a compound of formula I:

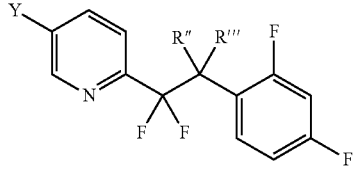

wherein R" is OH or OTMS;
R'" is CN or —CH₂NH₂;
Y is

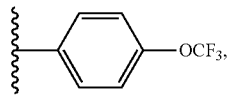 [SMILES: *c1ccc(OC(F)(F)F)cc1]

halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl;
alternatively R" and R'" may be taken together to form a carbonyl;
with the proviso that Y is not Br when R" and R'" are taken together to form a carbonyl.

In other aspects, the invention provides a compound of any of the formulae herein, wherein the compound inhibits (or is identified to inhibit) lanosterol demethylase (CYP51).

In another aspect, the invention provides a pharmaceutical composition comprising the compound of formula 1 and a pharmaceutically acceptable carrier.

In other aspects, the invention provides a method of modulating metalloenzyme activity in a subject, comprising contacting the subject with a compound of formula I, in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of formula I.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of formula I, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of formula I, such that metalloenzyme activity in said subject is modulated (e.g., down regulated, inhibited). In another aspect, the compounds delineated herein preferentially target cancer cells over nontransformed cells.

DETAILED DESCRIPTION

Definitions

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts". $J. Pharm. Sci.$ 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.: Jähnisch. K et al, Angew. Chem. Int. Ed. Engl. 2004 43: 406; and references therein). Additional reaction schemes and protocols may be determined by the skilled artesian by use of commercially available structure-searchable database software, for instance. SciFinder® (CAS division of the American Chemical Society) and CrossFire Beilstein® (Elsevier MDL), or by appropriate keyword searching using an internet search engine such as Google® or keyword databases such as the US Patent and Trademark Office text database. The invention includes the intermediate compounds used in making the compounds of the formulae herein as well as methods of making such compounds and intermediates, including without limitation those as specifically described in the examples herein.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. All salt, hydrate, and solvate forms of the compounds described herein are expressly included in the present invention. All ester and prodrug forms of the compounds described herein are included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers. e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Pharmaceutical Compositions

In one aspect, the invention provides a pharmaceutical composition comprising the compound of any of the formulae herein (e.g., Formula 1 or 1a) and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of formula I, in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, manitol, and polyethylene glycol; agar, alginic acids; pyrogen-free water; isotonic saline; and phosphate buffer solution; skim milk powder, as well as other non-toxic compatible substances used in pharmaceutical formulations such as Vitamin C, estrogen and *echinacea*, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407, 713; 5,352,456; 5,332,213; 5,336,168; 5,290,561; 5,254, 346; 5,164,189; 5,163,899; 5,088,977; 5,087,240; 5,008, 110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Agricultural Applications

The compounds and compositions herein can be used in methods of modulating metalloenzyme activity in a microorganism on a plant comprising contacting a compound (or composition) herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of 1 or 1a

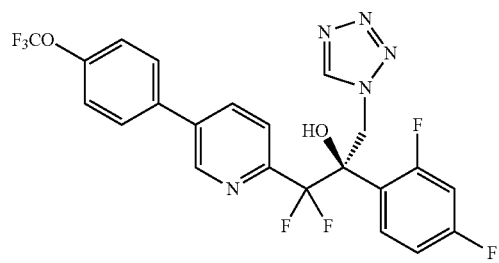

1

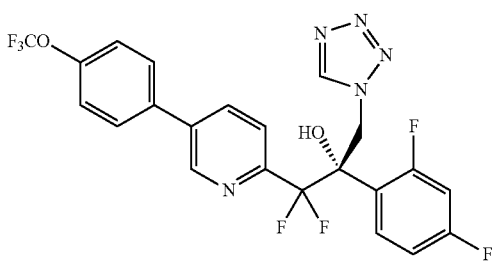

1a

A process to prepare enantiopure compound 1 or 1a is disclosed. Syntheses of 1 or 1a may be accomplished using the example syntheses that are shown below (Schemes 1-9). The preparation of precursor ketone 8 is performed starting with reaction of dibromo-pyridine 2-Br with ethyl 2-bromo-difluoroacetate to produce ester 3-Br. This ester is reacted with tetrazole reagent 4 via Claisen reaction to furnish 5-Br. Decarboxylation of 5-Br via a two-step process produces compound 6-Br. Suzukin coupling of 6-Br with boronate 7 furnishes 8.

Scheme 1. Synthesis of ketone 8

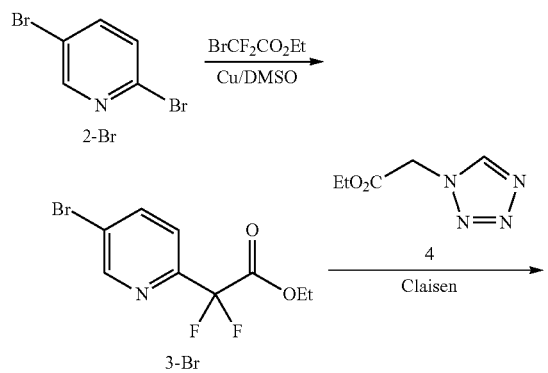

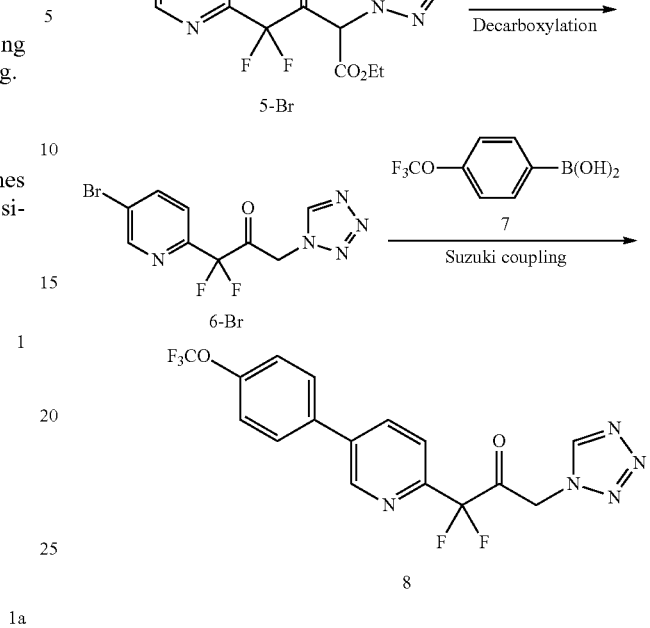

Ketone 8 may be prepared in an analogous fashion as described in Scheme 1 starting from corresponding substituted 2-bromo-pyridines, which can be prepared using according to synthetic transformations known in the art and contained in the references cited herein (Scheme 2).

Scheme 2. Synthesis of ketone 8

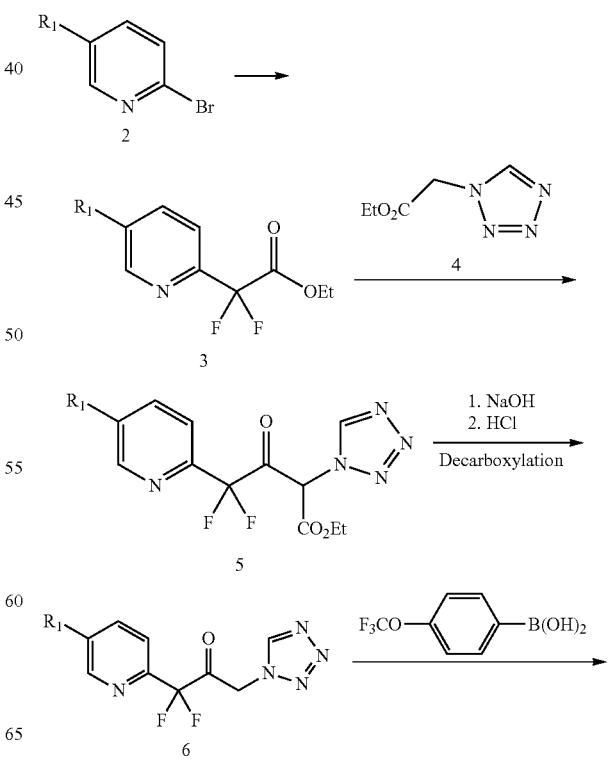

-continued

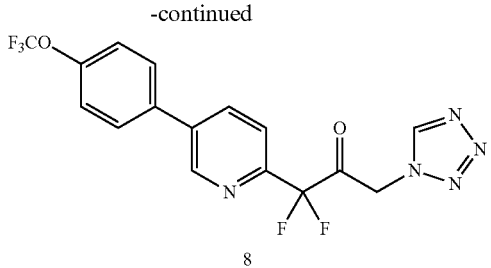

8

R₁ = halo, —O(C═O)-alkyl, —O(C═O)-substituted alkyl,
—O(C═O)-aryl, —O(C═O)-substituted aryl, —O(C═O)—O-alkyl,
—O(C═O)—O-substituted alkyl, —O(C═O)—O-aryl,
—O(C═O)—O-substituted aryl, —O(SO₂)-alkyl,
—O(SO₂)-substituted alkyl, —O(SO₂)-aryl, or —O(SO₂)-substituted aryl.

Compounds 6 or 8 may be reacted with a series of metallated derivatives of 2,4-difluoro-bromobenzene and chiral catalysts/reagents (e.g. BINOL) to effect enantiofacial-selective addition to the carbonyl group of 6 or 8 (Scheme 3). These additions can be performed on 6 or 8 to furnish 9 (or 9a, the enantiomer of 9, or mixtures thereof) or 1 (or 1a, the enantiomer of 1, or mixtures thereof), respectively.

Scheme 3. Synthesis of 1 or 1a

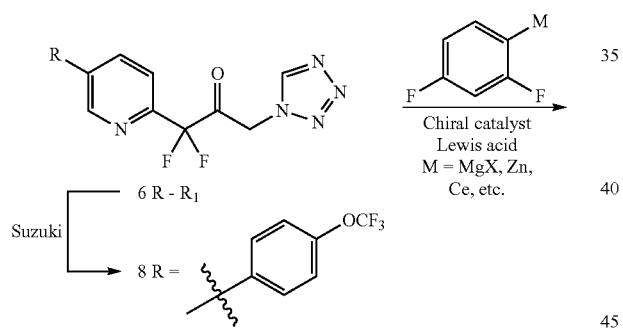

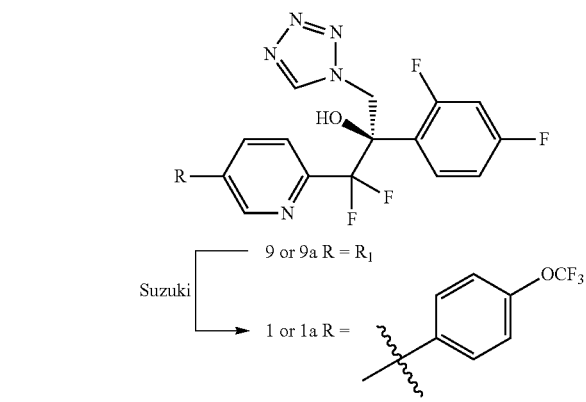

R₁ = halo, —O(C═O)-alkyl, —O(C═O)-substituted alkyl, —O(C═O)-aryl,
—O(C═O)-substituted aryl, —O(C═O)—O-alkyl,
—O(C═O)—O-substituted alkyl, —O(C═O)—O-aryl,
—O(C═O)—O-substituted aryl, —O(SO₂)-alkyl, —O(SO₂)-substituted alkyl,
—O(SO₂)-aryl, or —O(SO₂)-substituted aryl.

Alternatively, ketone 8 can be synthesized from aldehyde 10 (Scheme 4). Aldehyde 10 is coupled with 7 to produce 11. Compound 11 is then converted to 12 via treatment with diethylaminosulfurtrifluoride (DAST).

Scheme 4. Alternate synthesis of ketone 8

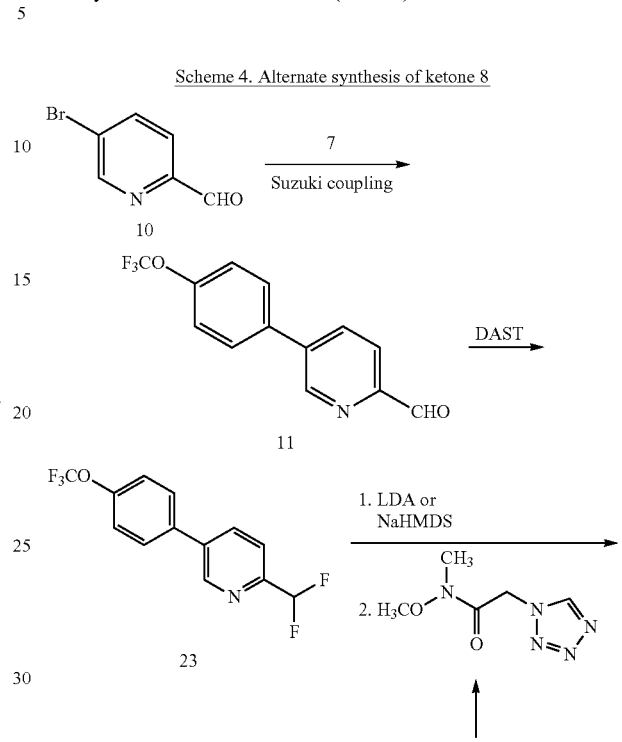

Scheme 5 outlines the synthesis of precursor ketone 15-Br. The ketone is prepared by conversion of 2-Br to 3-Br as described above. Next, ester 3-Br is converted to 15-Br by treatment via lithiation of 2,4-difluoro-bromobenzene.

Scheme 5. Synthesis of ketone 15-Br

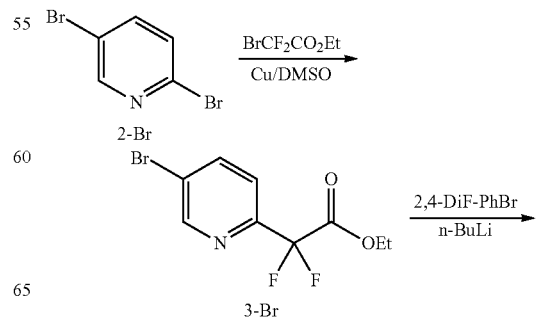

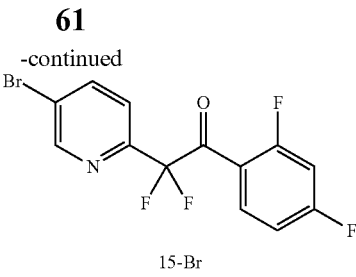

15-Br

Ketone 15 may be prepared in an analogous fashion as described for 15-Br in Scheme 5 starting from corresponding substituted 2-bromo-pyridines, which can be prepared using according to synthetic transformations known in the art and contained in the references cited herein (Scheme 6).

Scheme 6. Synthesis of ketone 15

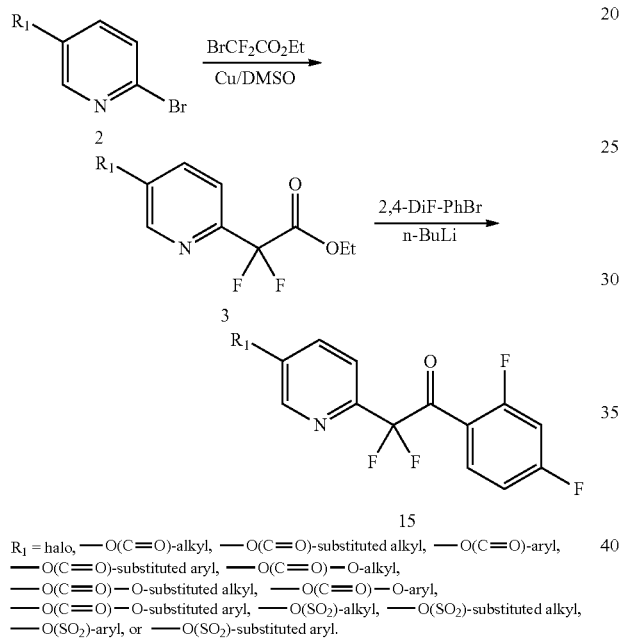

$R_1$ = halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

Ketone 15 may be used to prepare 9 (or 9a, the enantiomer of 9, or mixtures thereof) or 1 (or 1a, the enantiomer of 1, or mixtures thereof) by the following three-step process (Scheme 7). In the presence of a chiral catalyst/reagent (e.g. proline derivatives), base-treated nitromethane is added to 15 or 16 to furnish 17 (or 17a, the enantiomer of 17, or mixtures thereof) or 18 (or 18a, the enantiomer of 18, or mixtures thereof), respectively. Reduction of 17 (or 17a, the enantiomer of 17, or mixtures thereof) or 18 (or 18a, the enantiomer of 18, or mixtures thereof) (e.g. lithium aluminum hydride) produces 19 (or 19a, the enantiomer of 19, or mixtures thereof) or 20 (or 20a, the enantiomer of 20, or mixtures thereof). Annulation of 19 (or 19a, the enantiomer of 19, or mixtures thereof) or 20 (or 20a, the enantiomer of 20, or mixtures thereof) by treatment with sodium azide/triethylorthoformate furnishes tetrazoles 9 (or 9a, the enantiomer of 9, or mixtures thereof) or 1 (or 1a, the enantiomer of 1, or mixtures thereof). Suzuki coupling of 9 (or 9a, the enantiomer of 9, or mixtures thereof) with 4-trifluoromethoxyphenyl-boronic acid produces 1 (or 1a, the enantiomer of 1, or mixtures thereof).

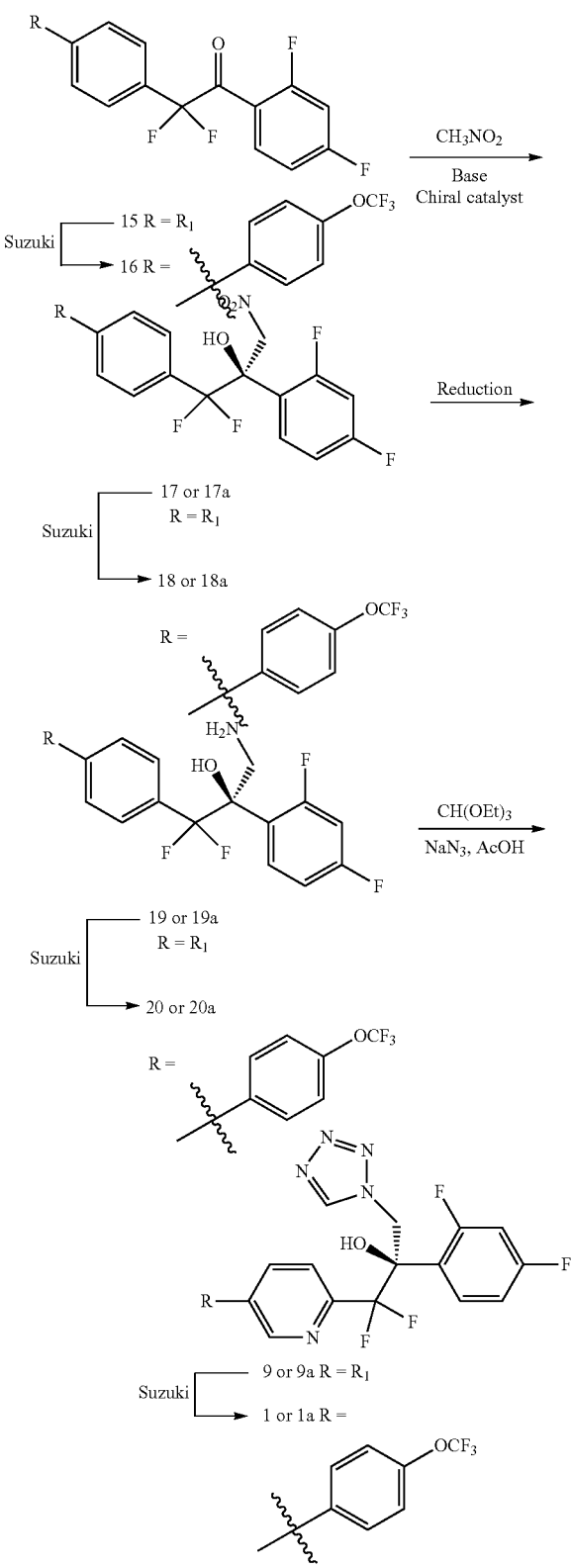

$R_1$ = halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

Ketone 21 may be employed to prepare optically-active epoxides via Horner-Emmons reaction of a difluoromethyl substrate to produce 22 or 22a. Ketones related to 21 have been prepared (M. Butters, *Org. Process Res. Dev.* 2001, 5, 28-36). Nucleophilic addition of metalated 5-(4-trifluoromethoxy)phenyl-2-pyridine (M=metal) to epoxide 22 or 22a may furnish compound 1 or 1a.

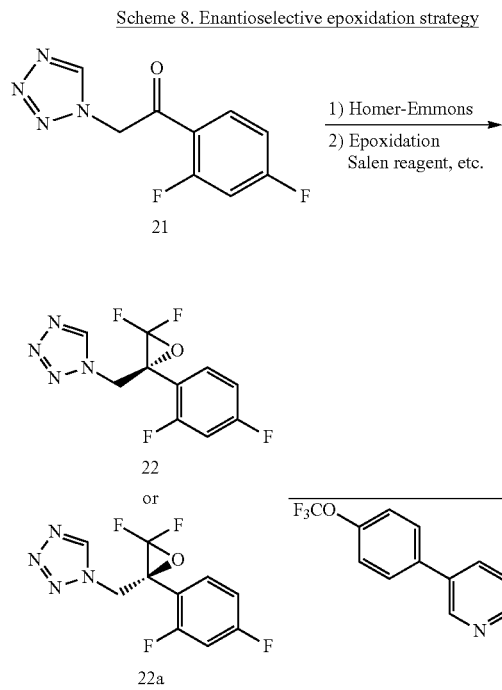

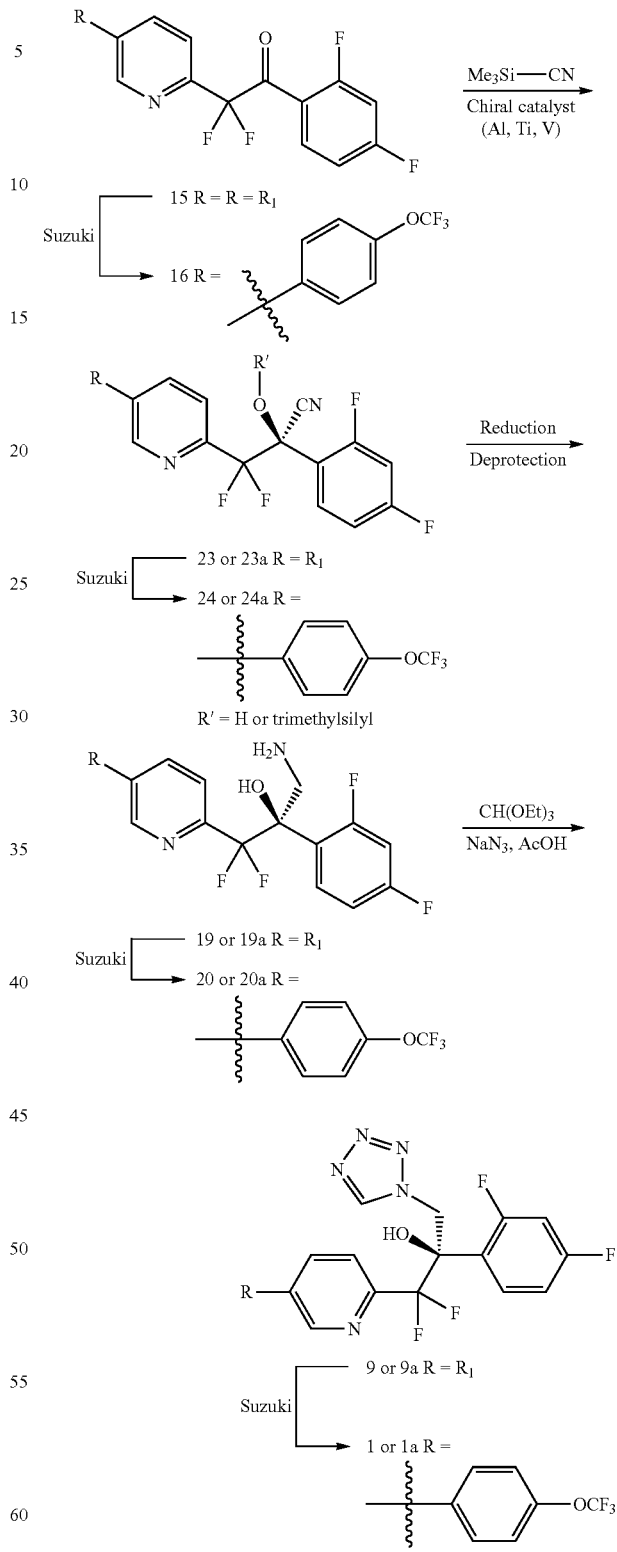

Ketone 15 or 16 may be used to prepare 9 (or 9a, the enantiomer of 9, or mixtures thereof) or 1 (or 1a, the enantiomer of 1, or mixtures thereof) by an alternative three-step process to Scheme 7 (Scheme 9). In the presence of a chiral catalyst/reagent, trimethylsilyl-cyanide is added to 15 or 16 to furnish 23 (or 23a, the enantiomer of 23, or mixtures thereof) or 24 (or 24a, the enantiomer of 24, or mixtures thereof), respectively (S. M. Dankwardt, *Tetrahedron Lett.* 1998, 39, 4971-4974). Reduction of 23 (or 23a, the enantiomer of 23, or mixtures thereof) or 24 (or 24a, the enantiomer of 24, or mixtures thereof) (e.g. lithium aluminum hydride) produces 19 (or 19a, the enantiomer of 19, or mixtures thereof) or 20 (or 20a, the enantiomer of 20, or mixtures thereof). Annulation of 19 (or 19a, the enantiomer of 19, or mixtures thereof) or 20 (or 20a, the enantiomer of 20, or mixtures thereof) by treatment with sodium azide/triethylorthoformate furnishes tetrazoles 9 (or 9a, the enantiomer of 9, or mixtures thereof) or 1 (or 1a, the enantiomer of 1, or mixtures thereof). Suzuki coupling of 9 (or 9a, the enantiomer of 9, or mixtures thereof) with 4-trifluoromethoxyphenyl-boronic acid produces 1 (or 1a, the enantiomer of 1, or mixtures thereof).

Example 1

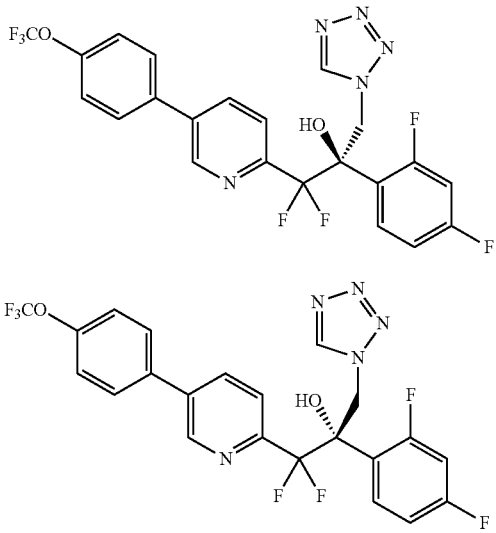

2-(2, 4-Difluorophenyl)-1,1-difluoro-3-(1H-tetrazol-1-yl)-1-(5-(4-(trifluoromethoxy)phenyl)pyridin-2-yl) propen-2-ol (1 or 1a)

White powder: $^1$H NMR (500 MHz, CDCl$_3$): δ 8.76 (s, 1 H), 8.70 (s, 1 H), 7.97 (dd, J=8.0, 2.0 Hz, 1 H), 7.68 (d, J=8.5 Hz, 1 H), 7.60-7.56 (m, 3H), 7.43-7.36 (m, 3 H), 6.80-6.76 (m, 1 H), 6.70-6.67 (m, 1 H), 5.57 (d, J=14.5 Hz, 1 H), 5.17 (d, J=14.5 Hz, 1 H). HPLC: 98.3%. Mass: m/z 513.9 [M$^+$+1]. HPLC: 99.8%. Optical rotation $[\alpha]_D^{25}$: +19° (C=0.1% in MeOH).

Intermediate 3-Br (R$_1$=Br)

To a clean and dry 100 L jacketed reactor was added copper powder (1375 g, 2.05 equiv, 10 micron, sphereoidal. SAFC Cat #326453) and DMSO (17.5 L, 7 vol). Next, ethyl bromodifluoroacetate (2.25 kg, 1.05 equiv. Apollo lot #102956) was added and the resulting slurry stirred at 20-25° C. for 1-2 hours. Then 2,5-dibromopyridine (2-Br, 2.5 kg, 1.0 equiv, Alfa Aesar lot # F14P38) was added to the batch and the mixture was immediately heated (using the glycol jacket) to 35° C. After 70 hours at 35° C., the mixture was sampled for CG/MS analysis. A sample of the reaction slurry was diluted with 1/1 CH$_3$CN/water, filtered (0.45 micron), and the filtrate analyzed directly. Ideally, the reaction is deemed complete if <5% (AUC) of 2,5-dibromopyridine remains. In this particular batch, 10% (AUC) of 2,5-dibromopyridine remained. However due to the already lengthy reaction time, we felt that prolonging the batch would not help the conversion any further. The reaction was then deemed complete and diluted with EtOAc (35 L). The reaction mixture was stirred at 20-35° C. for 1 hour and then the solids (copper salts) were removed by filtration through a pad of Celite. The residual solids inside the reactor were rinsed forward using EtOAc (2×10 L) and then this was filtered through the Celite. The filter cake was washed with additional EtOAc (3×10 L) and the EtOAc filtrates were combined. A buffer solution was prepared by dissolving NH$_4$Cl (10 kg) in DI water (100 L), followed by the addition of aqueous 28% NH$_4$OH (2.0 L) to reach pH=9. Then the combined EtOAc filtrates were added slowly to a pre-cooled (0 to 15 CC) solution of NH$_4$Cl and NH$_4$OH (35 L, pH=9) buffer while maintaining T<30° C. The mixture was then stirred for 15-30 minutes and the phases were allowed to separate. The aqueous layer (blue in color) was removed and the organic layer was washed with the buffer solution until no blue color was discernable in the aqueous layer. This experiment required 3×17.5 L washes. The organic layer was then washed with a 1/1 mixture of Brine (12.5 L) and the pH=9 NH$_4$Cl buffer solution (12.5 L), dried over MgSO$_4$, filtered, and concentrated to dryness. This provided crude compound 3-Br [2.29 kg, 77% yield, 88% (AUC) by GC/MS] as a yellow oil. The major impurity present in crude 3-Br was unreacted 2,5-dibromopyridine [10% (AUC) by GC/MS]. $^1$H NMR (CDCl$_3$) was consistent with previous lots of crude compound 3-Br. Crude compound 3-Br was then combined with similar purity lots and purified by column chromatography (5/95 EtOAc/heptane on SiO$_2$ gel).

Intermediate 15-Br (R$_1$=Br)

To a clean and dry 72 L round bottom flask was added 1-bromo-2,4-difluorobenzene (1586 g, 1.15 equiv. Oakwood lot # H4460) and MTBE (20 L, 12.6 vol). This solution was cooled to −70 to −75° C. and treated with n-BuLi (3286 mL, 1.15 equiv, 2.5 M in hexanes, SAFC lot #32799MJ), added as rapidly as possible while maintaining −75 to −55° C. This addition typically required 35-45 minutes to complete. (NOTE: If the n-BuLi is added slowly, an white slurry will form and this typically gives poor results). After stirring at −70 to −65 OC for 45 minutes, a solution of compound 3-Br (2000 g, 1.0 equiv. AMRI lot #15CL049A) in MTBE (3 vol) was added rapidly (20-30 min) by addition funnel to the aryl lithium solution while maintaining −75 to −55° C. After stirring for 30-60 minutes at −75 to −55° C., the reaction was analyzed by GC/MS and showed only trace (0.5% AUC) 1-bromo-2,4-difluorobenzene present. The reaction was slowly quenched with aqueous 2 M HCl (3.6 L) and allowed to warm to room temperature. The mixture was adjusted to pH=6.5 to 8.5 using NaHCO$_3$ (4 L), and the organic layer was separated. The MTBE layer was washed with brine (5% NaCl in water, 4 L), dried over MgSO$_4$, filtered, and concentrated. In order to convert the intermediate hemi-acetal to 4-Br, the crude mixture was heated inside the 20 L rotovap flask at 60-65° C. for 3 hours (under vacuum), at this point all the hemi-acetal was converted to the desired ketone 4 by $^1$H NMR (CDCl$_3$). This provided crude compound 4-Br [2.36 kg, 75% (AUC) by HPLC] as a brown oil that solidified upon standing. This material can then be used "as-is" in the next step without further purification.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A process to prepare compound 1 or 1a, or a mixture thereof; or a salt of compound 1 or 1a, or a mixture thereof:

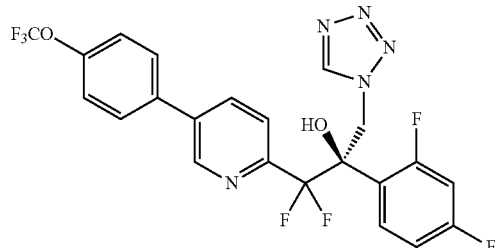

1

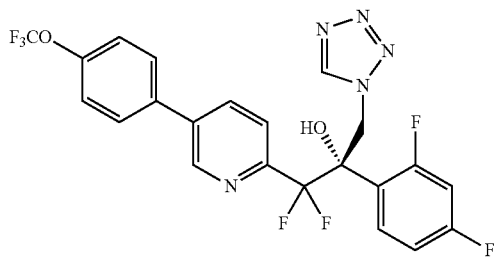

1a the process comprising nitromethylating a compound of formula 15:

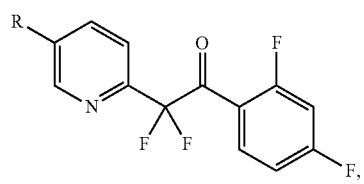

to provide a compound of formula 17 or 17a,

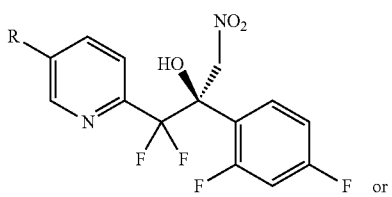

or

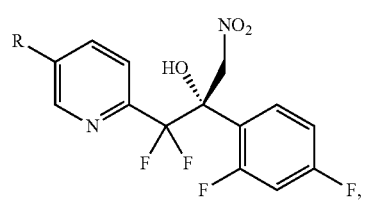

or a mixture thereof; and converting a compound of formula 17 or 17a,

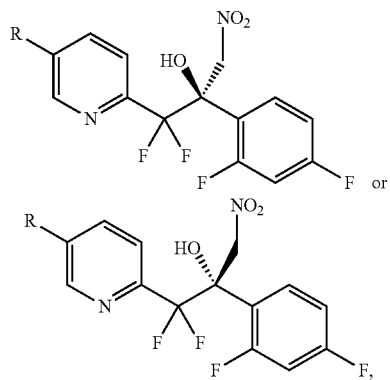

or a mixture thereof, to compound 1 or 1a, or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

2. The process of claim 1 comprising:
(i) reducing a compound of formula 17 or 17a,

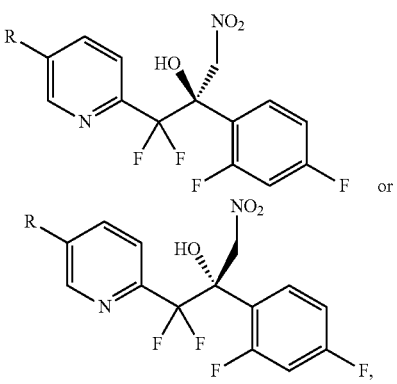

or a mixture thereof, to provide a compound of formula 19 or 19a,

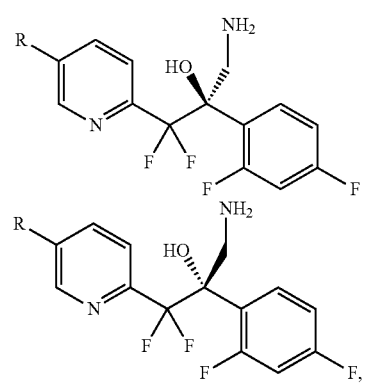

or a mixture thereof;

(ii) forming the tetrazole of a compound of formula 19 or 19a,

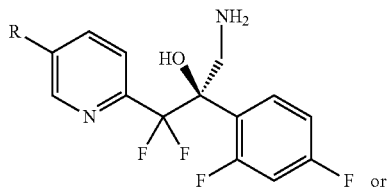

or

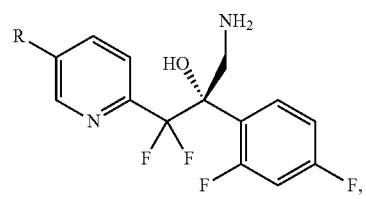

or a mixture thereof, to provide a compound of formula 9 or 9a,

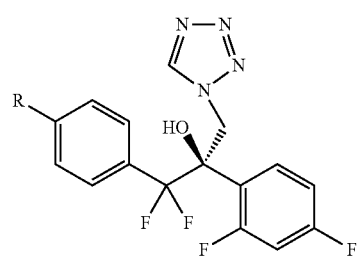

or a mixture thereof; and
(iii) arylating a compound of formula 9 or 9a,

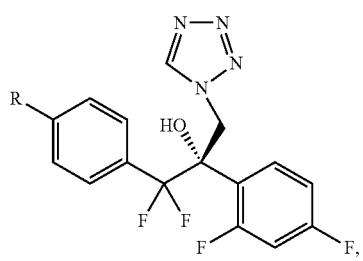

or

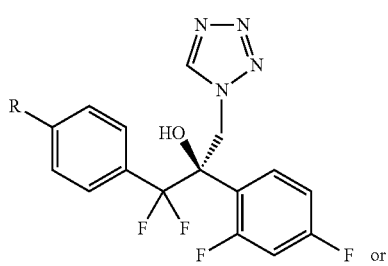

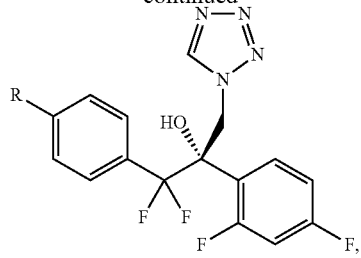

or a mixture thereof, to provide compound 1 or 1a,

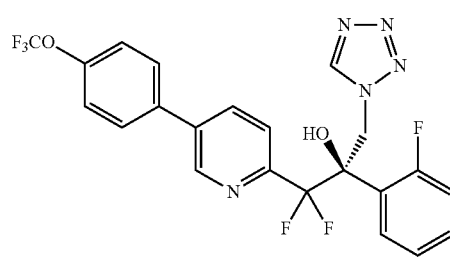

or

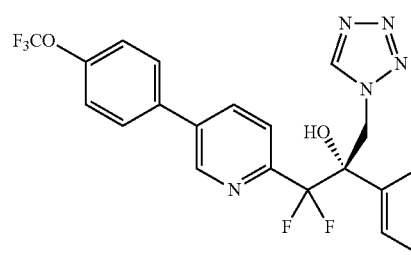

or a mixture thereof;

wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

3. A process to prepare compound 1 or 1a, or a mixture thereof; or a salt of compound 1 or 1a, or a mixture thereof:

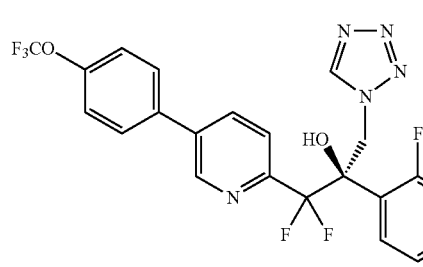

1

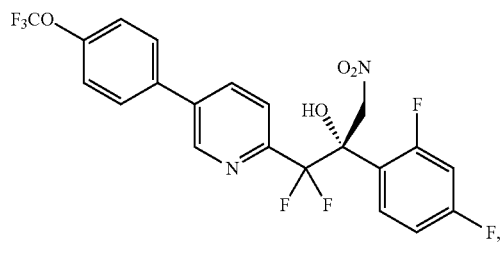
the process comprising:
(i) arylating a compound of formula 15,
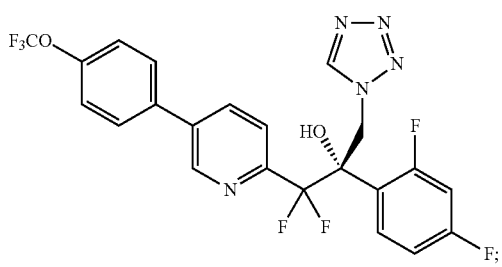
to provide ketone
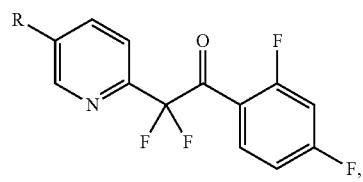
(ii) nitromethylating ketone 16,
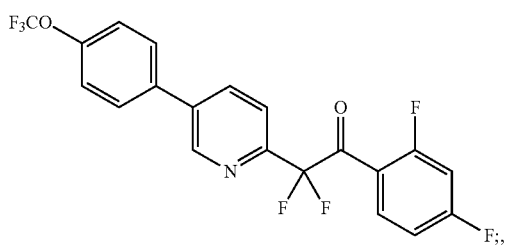
to provide nitro-alcohol 18 or 18a,
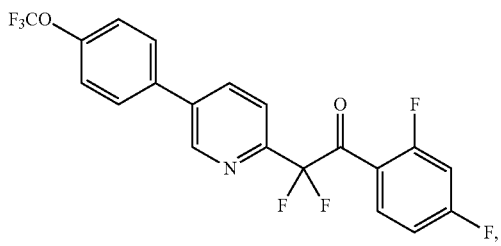 [SMILES: O=C(c1ccc(F)cc1F)C(F)(F)c1ccc(-c2ccc(OC(F)(F)F)cc2)cn1]
or a mixture thereof;
(iii) reducing nitro-alcohol 18 or 18a,
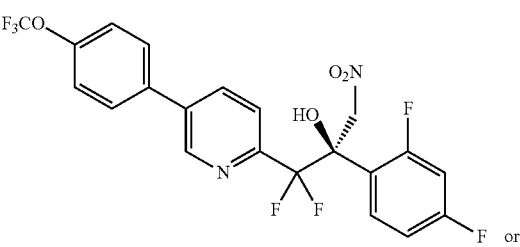
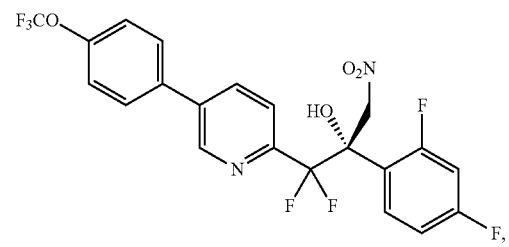
or a mixture thereof, to provide amino-alcohol 20 or 20a
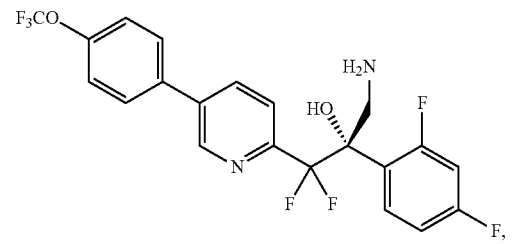
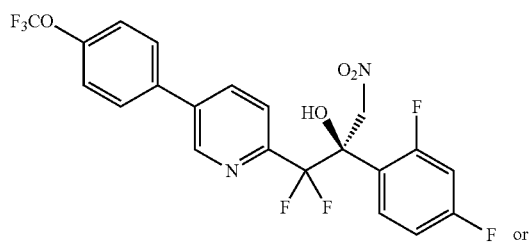
or a mixture thereof; and (iv) forming the tetrazole of amino-alcohol 20 or 20a,

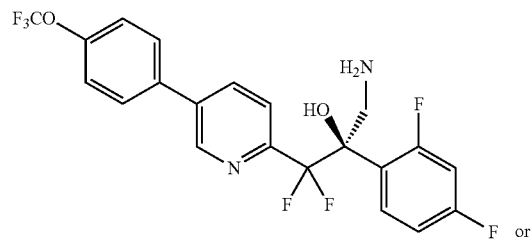

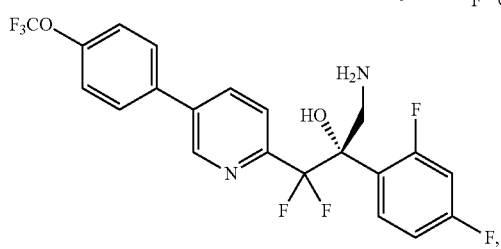

or a mixture thereof, to provide compound 1 or 1a,

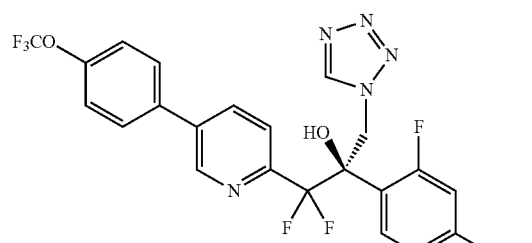

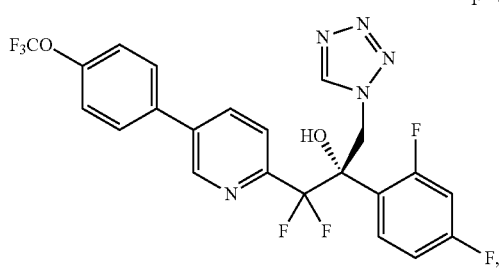

or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

4. The process of claim 1 comprising:

(i) arylating a compound of formula 17 or 17a,

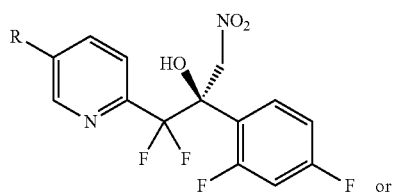

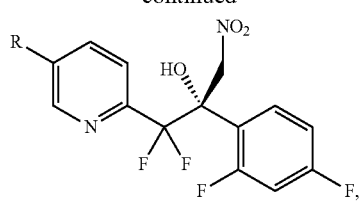

or a mixture thereof, to provide nitro-alcohol 18 or 18a,

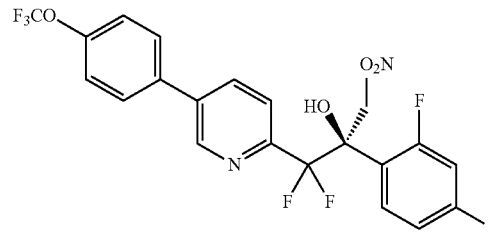

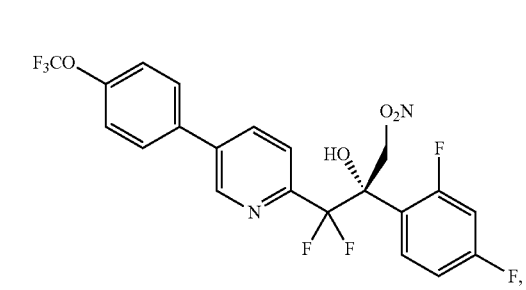

or a mixture thereof;

(ii) reducing nitro-alcohol 18 or 18a,

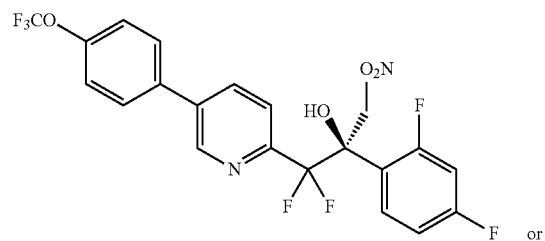

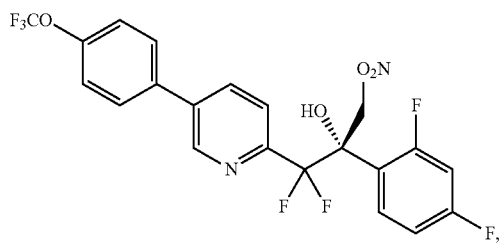

or a mixture thereof, to provide amino-alcohol 20 or 20a,

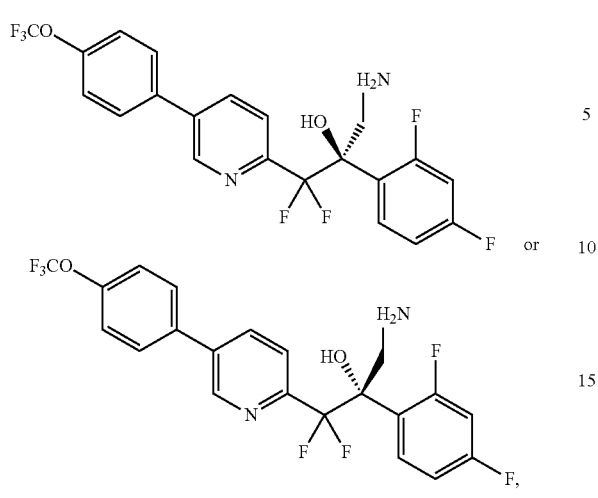

or a mixture thereof; and
(iii) forming the tetrazole of amino-alcohol 20 or 20a

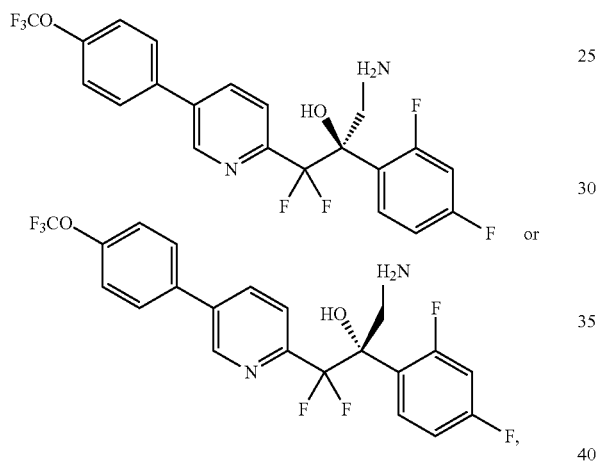

or a mixture thereof, to provide compound 1 or 1a,

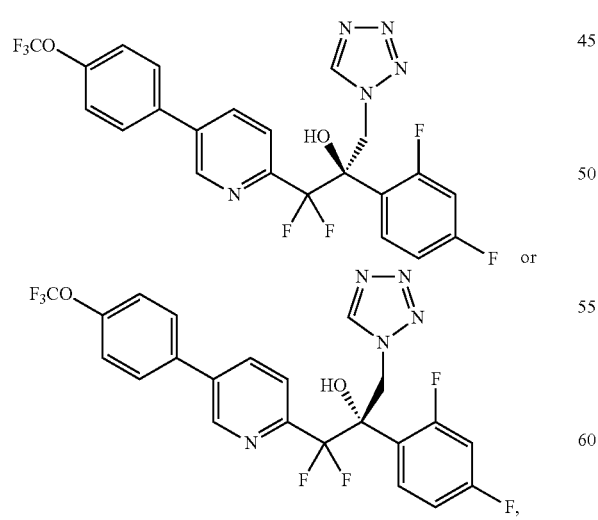

or a mixture thereof;
wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO₂)-alkyl, —O(SO₂)-substituted alkyl, —O(SO₂)-aryl, or —O(SO₂)-substituted aryl.

5. The process of claim 1 comprising:
(i) reducing a compound of formula 17 or 17a,

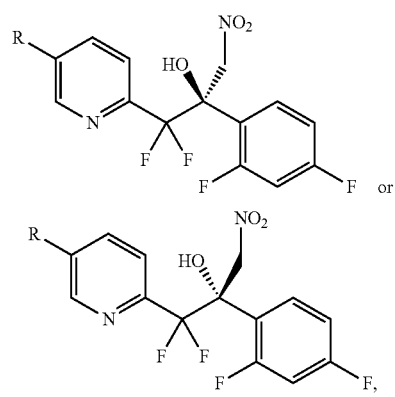

or a mixture thereof, to provide a compound of formula 19 or 19a,

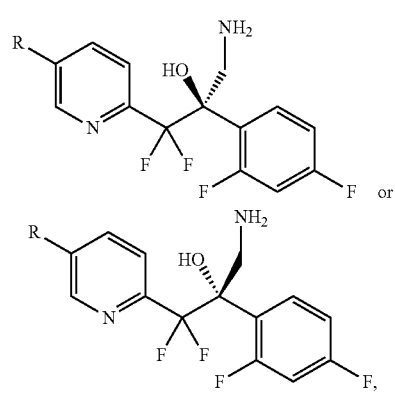

or a mixture thereof;
(ii) arylating a compound of formula 19 or 19a,

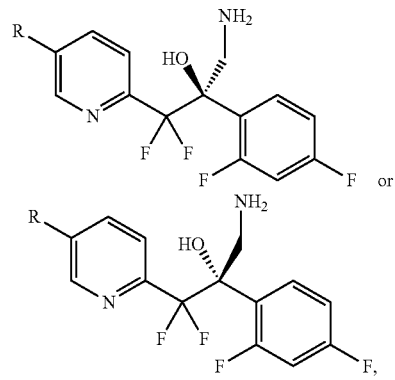

or a mixture thereof, to provide amino-alcohol 20 or 20a,

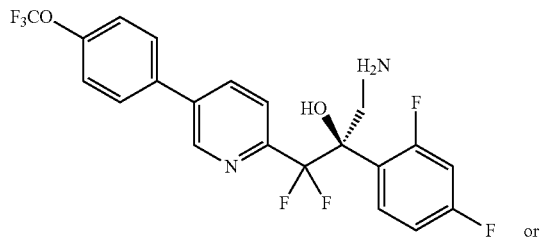

or

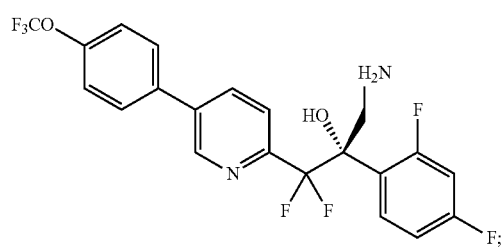

and (iii) forming the tetrazole of amino-alcohol 20 or 20a,

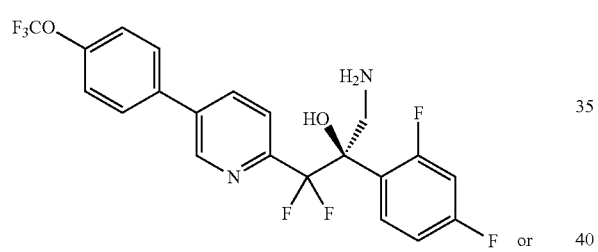

or

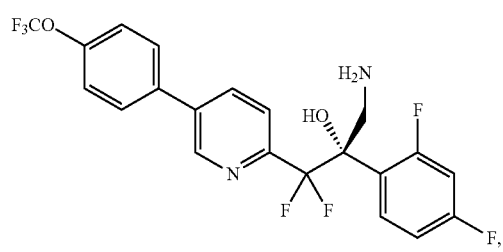

or a mixture thereof, to provide compound 1 or 1a,

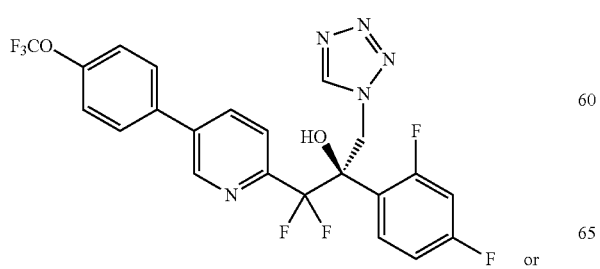

or

-continued

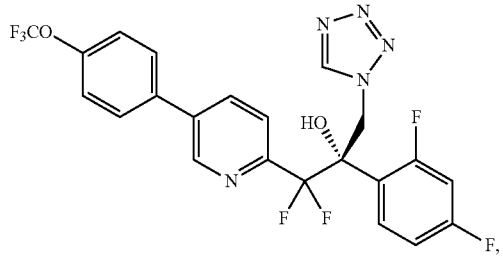

or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

6. A process to prepare compound 1 or 1a, or a mixture thereof; or a salt of compound 1 or 1a, or a mixture thereof:

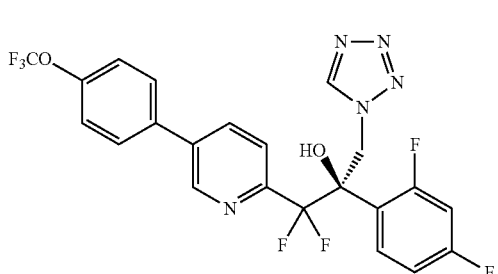

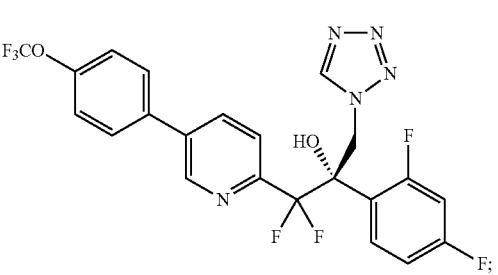

the process comprising:

(i) arylating a compound of formula 15,

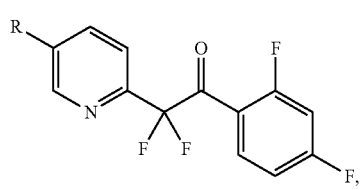

to provide ketone 16,
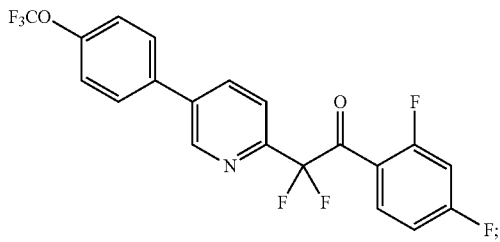 [SMILES: O=C(c1ccc(F)cc1F)C(F)(F)c1ccc(-c2ccc(OC(F)(F)F)cc2)cn1]
(ii) forming the cyanohydrin of ketone 16,
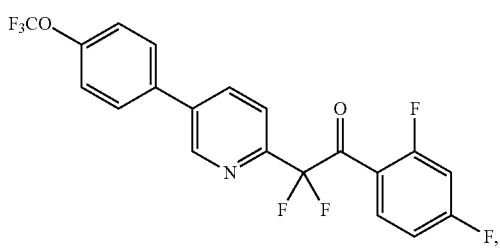 [SMILES: O=C(c1ccc(F)cc1F)C(F)(F)c1ccc(-c2ccc(OC(F)(F)F)cc2)cn1]
to provide nitrile 24 or 24a,
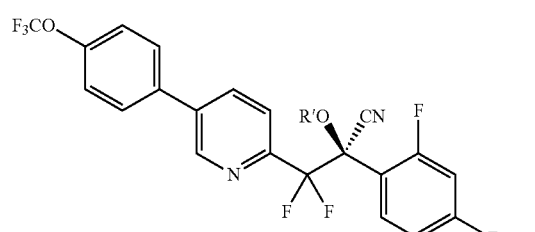
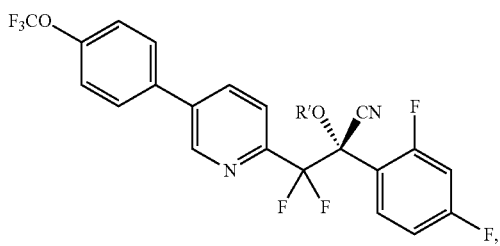
or a mixture thereof;
(iii) reducing nitrile 24 or 24a
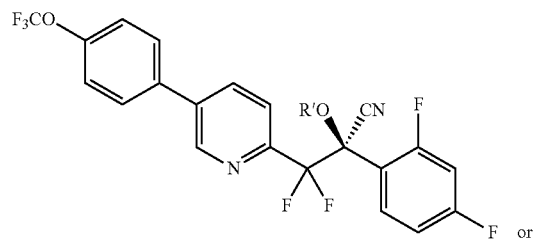
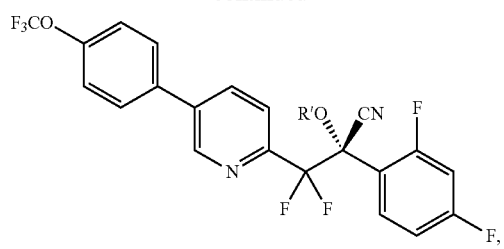
or a mixture thereof, to provide amino-alcohol 20 or 20a,
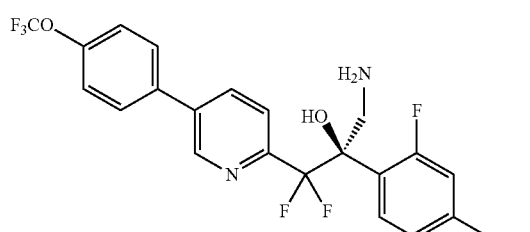
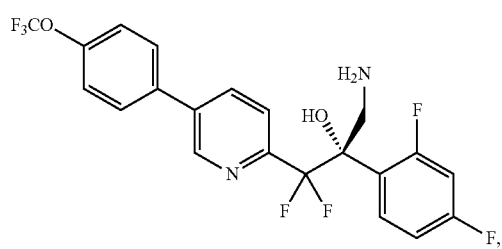
or a mixture thereof; and
(iv) forming the tetrazole of amino-alcohol 20 or 20a,
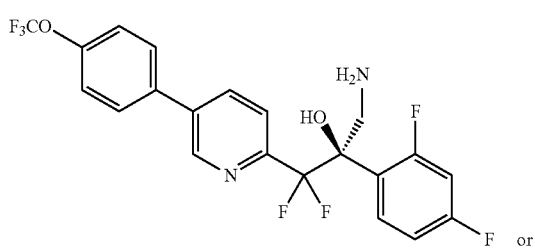
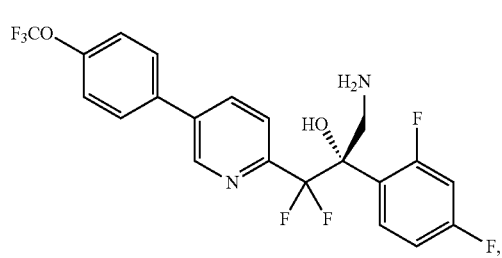
or a mixture thereof, to provide compound 1 or 1a,

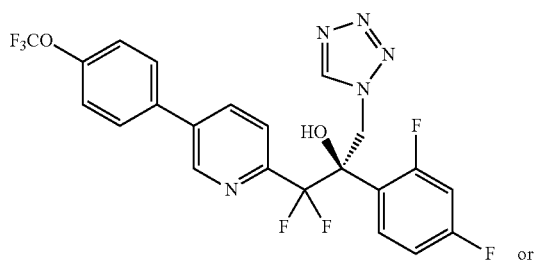

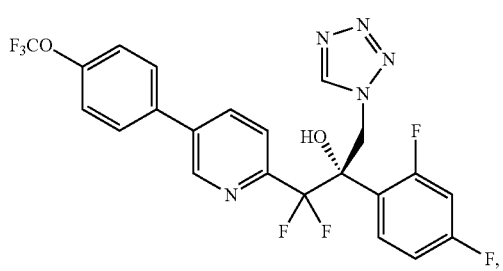

or a mixture thereof;

wherein R is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl; and R' is H or trimethylsilyl.

7. A process to prepare compound 1 or 1a, or a mixture thereof; or a salt of compound 1 or 1a, or a mixture thereof:

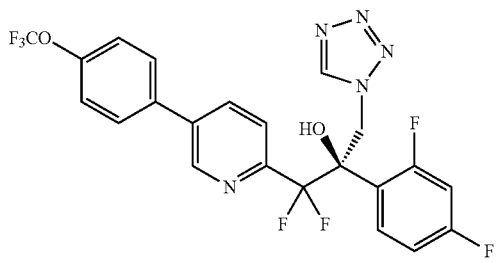

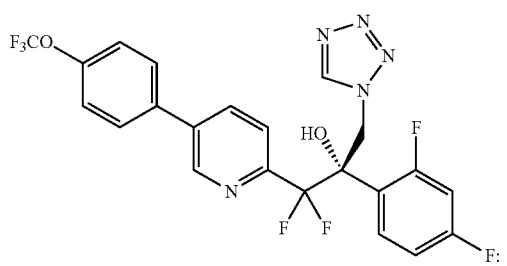

the process comprising:

cyanating a compound of formula 15,

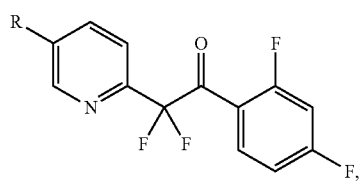

to provide a compound of formula 23 or 23a,

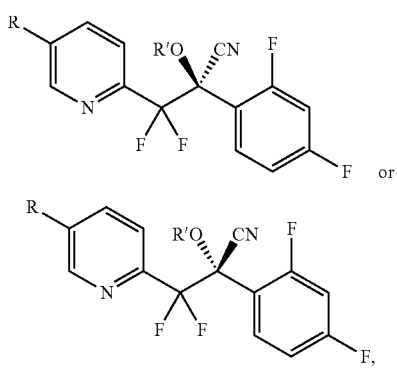

or a mixture thereof; and converting a compound of formula 23 or 23a,

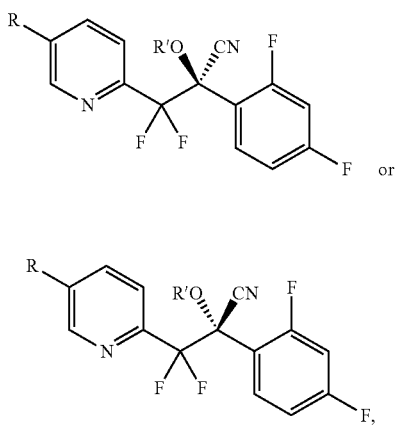

or a mixture thereof, to provide compound 1 or 1a,

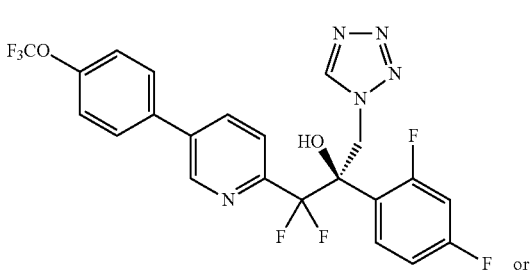

-continued

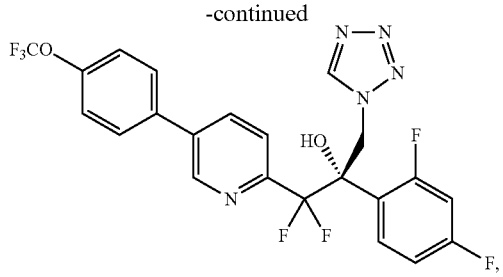

or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl; and R' is H or trimethylsilyl.

8. The process of claim 7 comprising:

(i) reducing a compound of formula 23 or 23a,

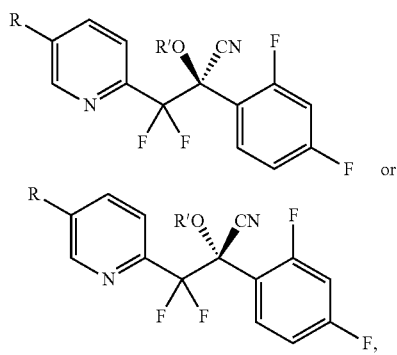

or a mixture thereof, to provide a compound of formula 19 or 19a,

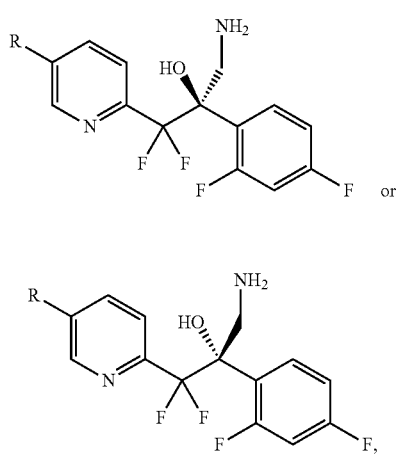

or a mixture thereof;

(ii) arylating a compound of formula 19 or 19a,

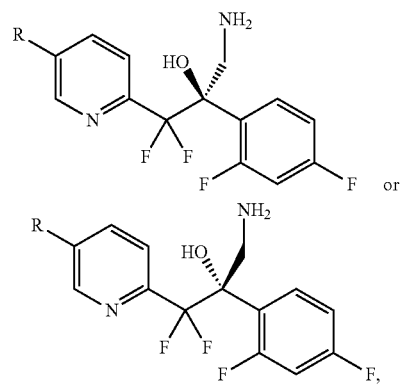

or a mixture thereof, to provide amino-alcohol 20 or 20a,

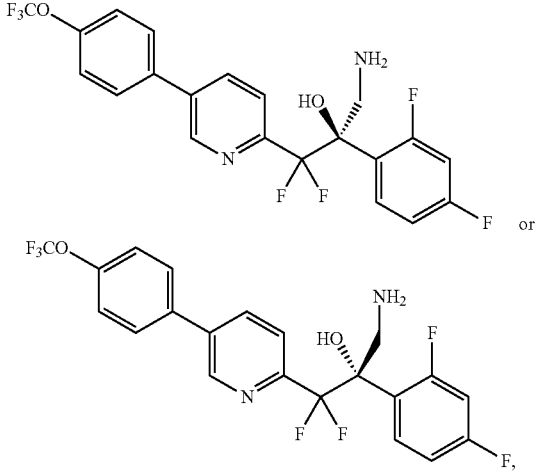

or a mixture thereof;

(iii) forming the tetrazole of amino-alcohol 20 or 20a,

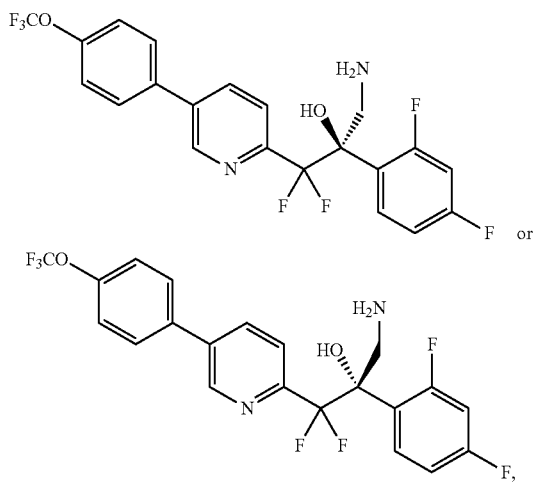

or a mixture thereof, to provide compound 1 or 1a

85

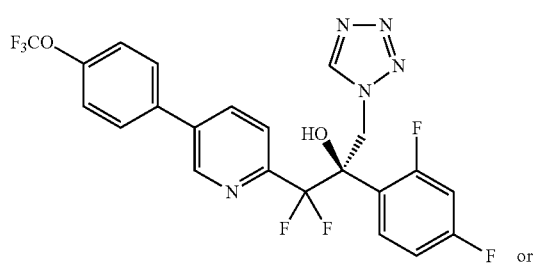

or

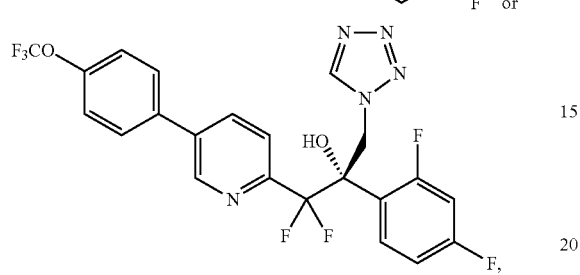

or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl; and R' is H or trimethylsilyl.

9. The process of claim 7 comprising:

(i) reducing a compound of formula 23 or 23a,

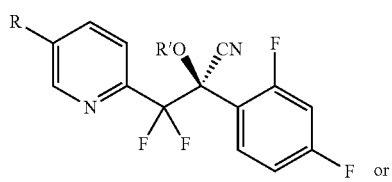

or

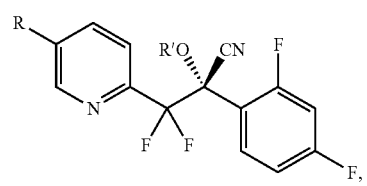

or a mixture thereof, to provide a compound of formula 19 or 19a,

86

-continued

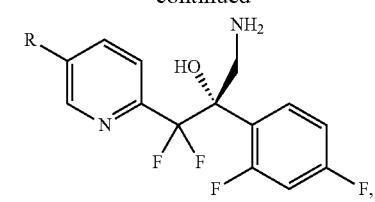

or a mixture thereof;

(ii) forming the tetrazole of a compound of formula 19 or 19a,

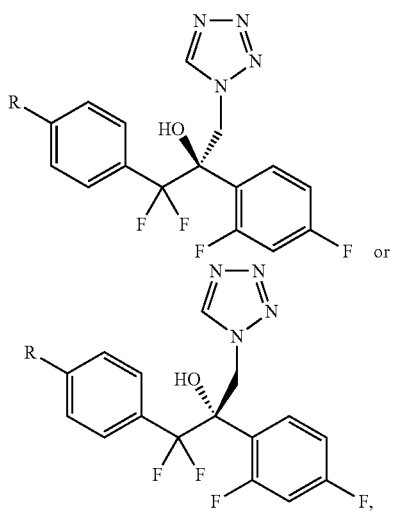

or a mixture thereof, to provide a compound of formula 9 or 9a,

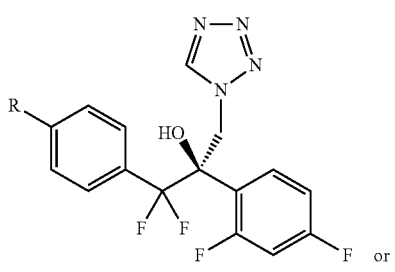

or a mixture thereof;

(iii) arylating a compound of formula 9 or 9a,

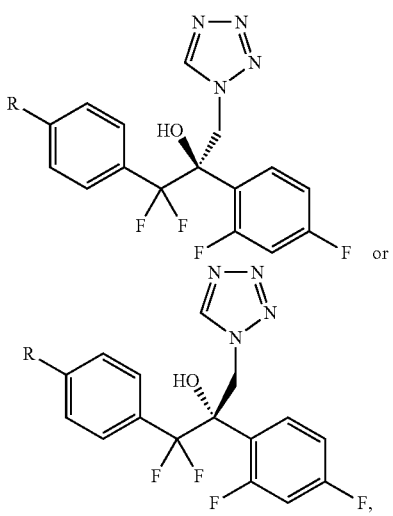

or a mixture thereof, to provide compound 1 or 1a,

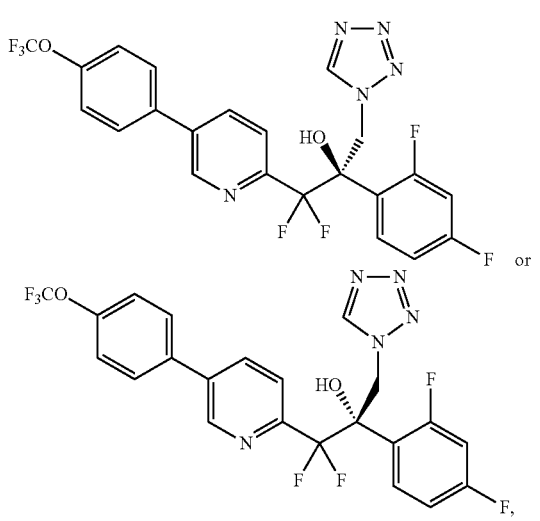

or a mixture thereof;
wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl; and
R' is H or trimethylsilyl.

10. The process of claim 7, comprising:
(i) arylating a compound of formula 23 or 23a,

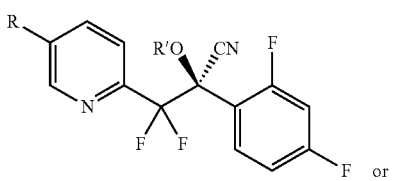

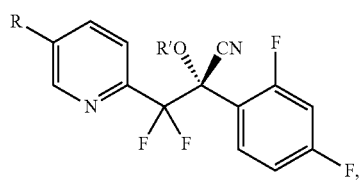

or a mixture thereof, to provide nitrile 24 or 24a,

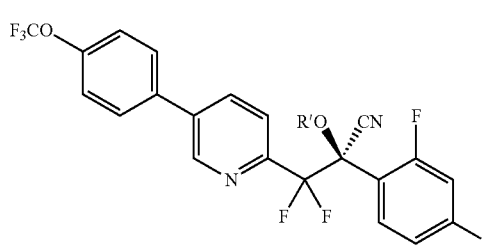

or a mixture thereof;
(ii) reducing nitrile 24 or 24a,

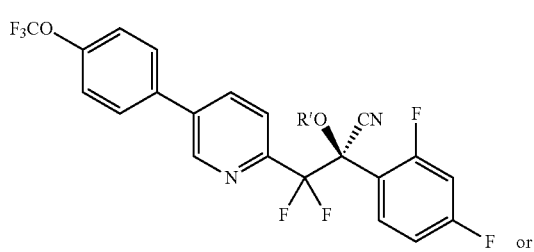

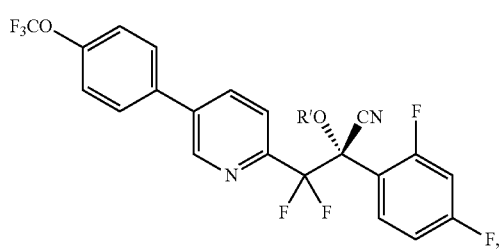

or a mixture thereof, to provide amino-alcohol 20 or 20a,

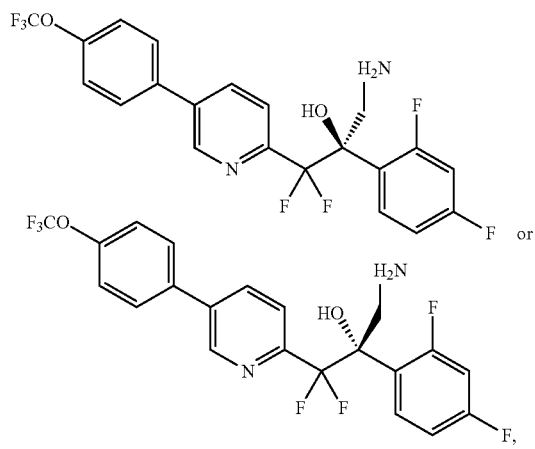

or a mixture thereof;
(iii) forming the tetrazole of amino-alcohol 20 or 20a,

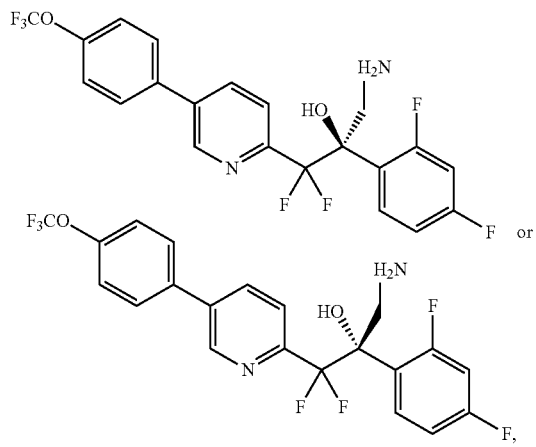

or a mixture thereof, to provide compound 1 or 1a,

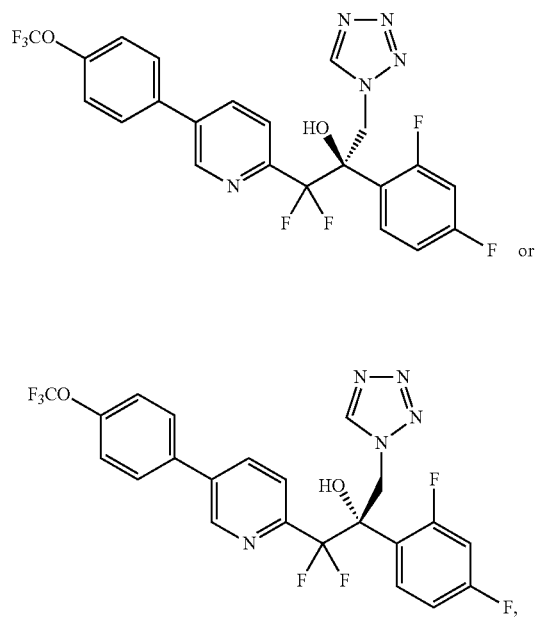

or a mixture thereof;

wherein R is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl; and R' is H or trimethylsilyl.

* * * * *